(12) United States Patent
Pierce, II et al.

(10) Patent No.: US 11,806,177 B2
(45) Date of Patent: Nov. 7, 2023

(54) NONCOLLIMATED SINGLE-PHOTON EMISSION COMPUTED TOMOGRAPHY

(71) Applicant: University of Washington, Seattle, WA (US)

(72) Inventors: Larry A. Pierce, II, Seattle, WA (US); Robert S. Miyaoka, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 17/910,343

(22) PCT Filed: Mar. 8, 2021

(86) PCT No.: PCT/US2021/021398
§ 371 (c)(1),
(2) Date: Sep. 8, 2022

(87) PCT Pub. No.: WO2021/183454
PCT Pub. Date: Sep. 16, 2021

(65) Prior Publication Data
US 2023/0181128 A1 Jun. 15, 2023

Related U.S. Application Data

(60) Provisional application No. 63/145,079, filed on Feb. 3, 2021, provisional application No. 62/987,798, filed on Mar. 10, 2020.

(51) Int. Cl.
*A61B 5/05* (2021.01)
*G01T 1/161* (2006.01)
(Continued)

(52) U.S. Cl.
CPC ............ *A61B 6/037* (2013.01); *A61B 6/4233* (2013.01); *A61B 6/5205* (2013.01)

(58) Field of Classification Search
CPC ....... A61B 6/037; A61B 6/4208; A61B 6/032; A61B 6/5217; A61B 34/10; A61B 6/4233
See application file for complete search history.

(56) References Cited

U.S. PATENT DOCUMENTS

| 4,377,752 A | 3/1983 | Sano et al. |
| 7,439,514 B1 | 10/2008 | Uribe et al. |

(Continued)

FOREIGN PATENT DOCUMENTS

| JP | H0862124 A | 3/1996 |
| WO | WO0122120 A1 | 3/2001 |

(Continued)

OTHER PUBLICATIONS

Audenhaege, et al., "Review of SPECT Collimator Selection, Optimization, and Fabrication for Clinical and Preclinical Imaging," Medical Physics, 42(8), Aug. 2015, pp. 4796-4813.

(Continued)

*Primary Examiner* — Don K Wong
(74) *Attorney, Agent, or Firm* — Lee & Hayes, P.C.

(57) ABSTRACT

Various noncollimated single photon emission computed tomography (SPECT) technologies are described herein. An example device includes an array of detectors configured to detect a flux of first photons transmitted from a field of view (FOV) over time. The device also includes an attenuator disposed between the array of detectors and the FOV. The attenuator is configured to move over time and to attenuate second photons emitted from the source. In various implementations, the attenuator is not a collimator. Based on the fluxes of the first photons detected by the detectors, and the position of the attenuator over time, an imaging system may be configured to generate an image of the FOV.

20 Claims, 8 Drawing Sheets

(51) Int. Cl.
*A61B 6/03* (2006.01)
*A61B 6/00* (2006.01)

(56) References Cited

U.S. PATENT DOCUMENTS

| | | |
|---|---|---|
| 7,831,024 B2 | 11/2010 | Metzler et al. |
| 10,067,239 B2 | 9/2018 | Nelson et al. |
| 2003/0178559 A1 | 9/2003 | Hamill et al. |
| 2019/0145895 A1 | 5/2019 | Livingston |

FOREIGN PATENT DOCUMENTS

| | | | |
|---|---|---|---|
| WO | WO2016201131 A1 | 12/2016 | |
| WO | WO-2018194937 A1 * | 10/2018 | ............. A61B 6/032 |

OTHER PUBLICATIONS

Bailey, et al., "An Evidence-Based Review of Quantitative SPECT Imaging and Potential Clinical Applications," Journal of Nuclear Medicine, 54 (1), Jan. 2013, pp. 83-89.

Gagnon, et al., "Design Considerations for a New Solid-State Gamma-Camera: SOLSTICE," Nuclear Science Symposium Conference Record, IEEE, vol. 2, Dec. 2001, pp. 1156-1160.

Hildebrandt, et al, "Molecular Imaging Applications for Immunology," Clinical Immunology, vol. 111, Issue 2, May 2004, pp. 210-224.

Joshi, B., "Medical Imaging Instrumentation: Global Markets and Technologies Through 2022," PR Newswire, Dec. 10, 2018, 2 pages.

Knipe, H., "Linear Attenuation Coefficient," Radiopaedia.org, Mar. 2020, 1 page.

Madsen, M. T., et al. "Recent Advances in SPECT Imaging," The Journal of Nuclear Medicine, 48(4), Apr. 2007, pp. 661-673.

International Search Report and Written Opinion for PCT Application No. PCT/US2021/021398, dated Jun. 30, 2021, 9 pages.

Perez-Roman, et al., "Use of Single-Photon Emission Computed Tomography Imaging for Hypermetabolic Facet Identification in Diagnosis of Cervical and Axial Back Pain," World Neurosurgery, vol. 137, May 2020, pp. e487-e492.

Schramm, et al., "Compact High Resolution Detector for Small Animal SPECT," IEEE Transactions on Nuclear Science, vol. 47, No. 3, Jun. 2000, pp. 1163-1167.

Schramm, et al., "High-Resolution SPECT Using Multipinhole Collimation," IEEE Transactions on Nuclear Science, vol. 50, No. 3, Jun. 2003, pp. 315-320.

Wang, et al., "Astigmatic Single Photon Emission Computed Tomography Imaging with a Displaced Center of Rotation," Medical Physics, vol. 25, Issue 8, Aug. 1998, pp. 1493-1501.

Webb, et al., "Geometric Efficiency of a Rotating Slit-Collimator for Improved Planar Gamma-Camera Imaging," Physics in Medicine & Biology, vol. 38, No. 5, May 1993, pp. 627-638.

* cited by examiner

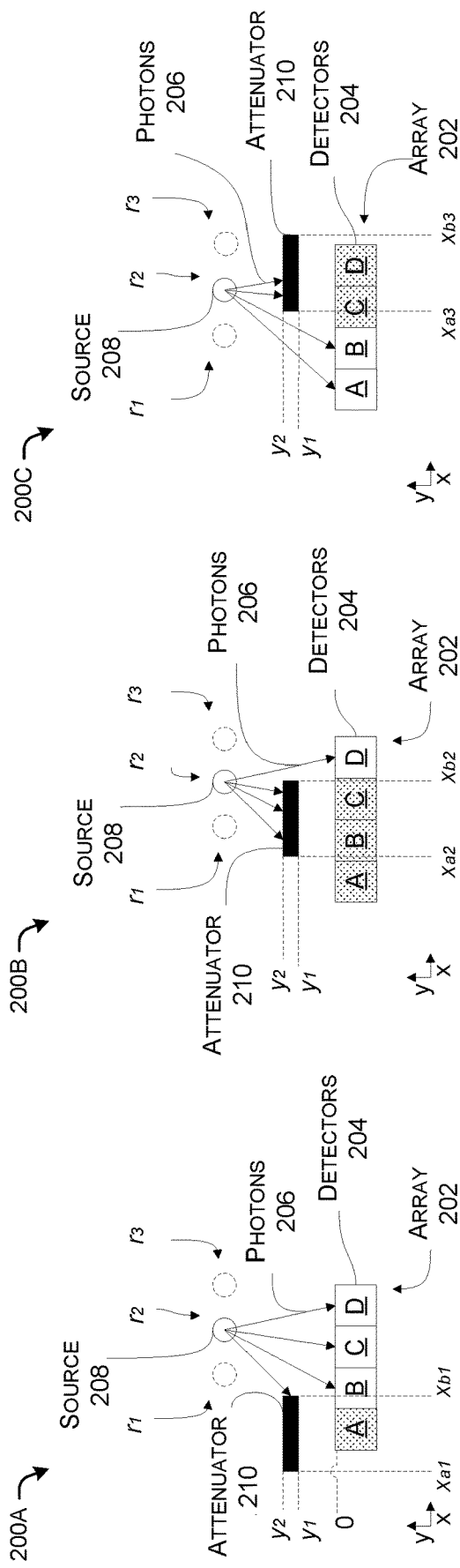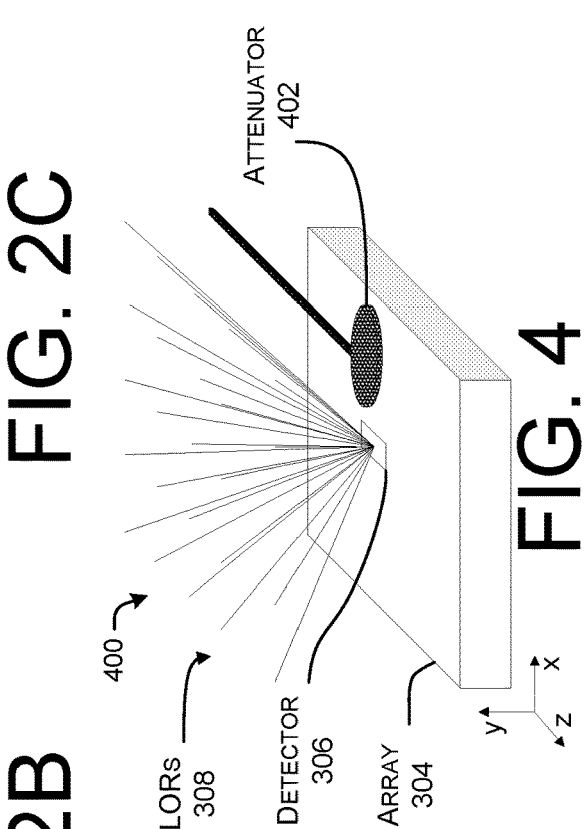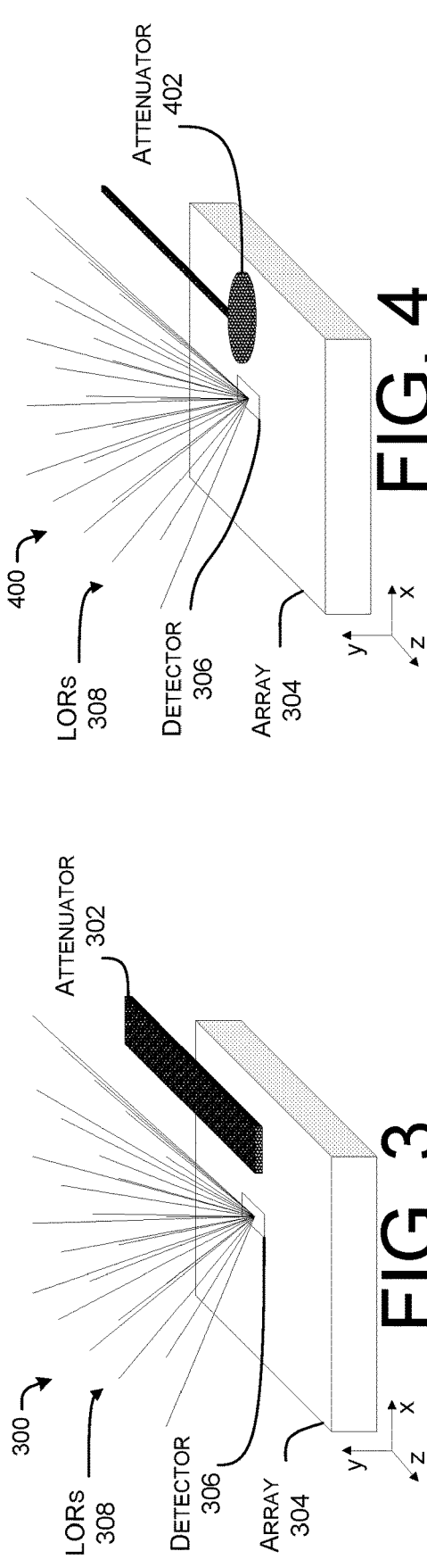

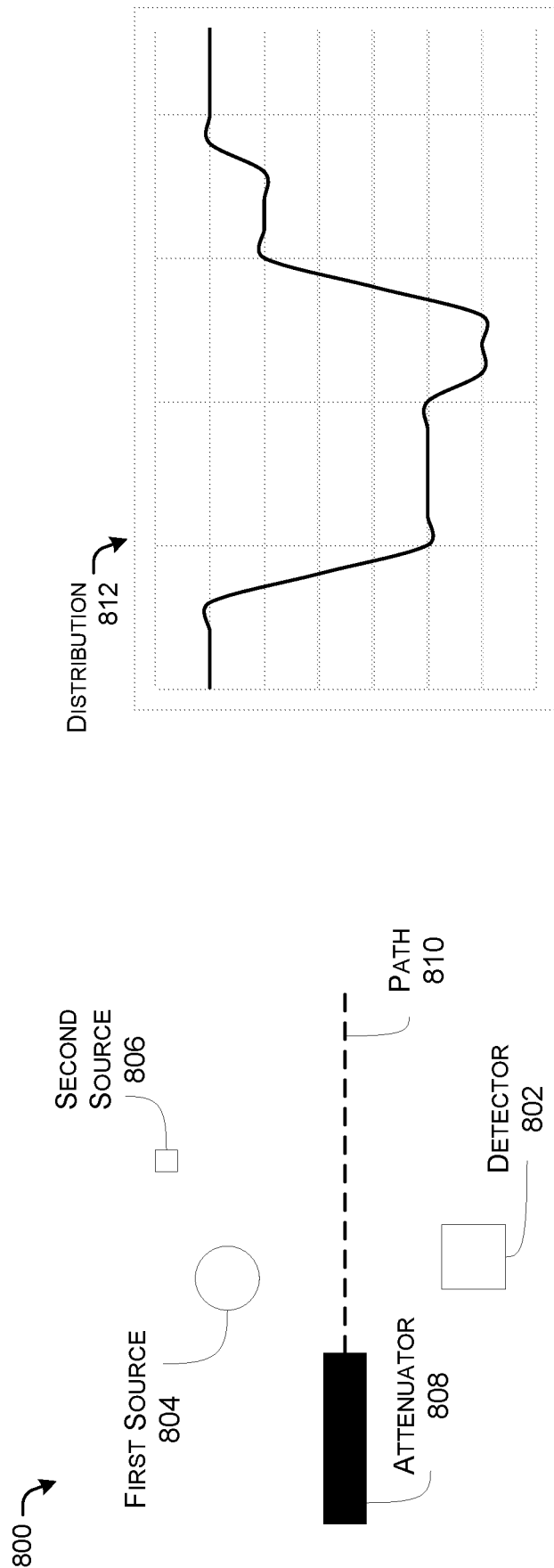

NONCOLLIMATED SINGLE-PHOTON EMISSION COMPUTED TOMOGRAPHY

CROSS-REFERENCE TO RELATED APPLICATIONS APPLICATION(S)

This application is a U.S. National Phase Application based on International Patent Application No. PCT/US2021/021398, filed on Mar. 8, 2021, which claims the priority of U.S. Provisional Application No. 62/987,798, filed on Mar. 10, 2020, and U.S. Provisional Application No. 63/145,079, filed on Feb. 3, 2021, each of which is incorporated by reference herein in its entirety.

TECHNICAL FIELD

This application relates to the technical field of medical imaging. In particular, this application describes improvements to Single-Photon Emission Computed Tomography (SPECT) and related imaging modalities.

BACKGROUND

SPECT is a major imaging modality in nuclear medicine. A conventional SPECT imaging system includes a gamma camera configured to detect photons emitted by a radiotracer, which may be injected or otherwise disposed in the body of a patient. The gamma camera is conventionally equipped with a collimator, which restricts the angle at which the photons are received by the gamma camera and prevents photons traveling at different angles from being detected by the gamma camera. A parallel hole collimator, for example, includes one or more parallel holes through which the photons are transmitted from the radiotracer to the gamma camera. Some examples utilize a converging hole collimator, which includes multiple holes extending along directions that converge at a focal point within the body of the patient or outside of the body of the patient. A pinhole collimator includes a small hole through an attenuating plate, wherein the photons from the radiotracer are transmitted through the hole and an image of the radiotracer is projected onto the gamma camera. Due to the presence of a collimator, the photons are received by the gamma camera at known angles. As a result, an image of the radiotracer can be derived based on the total amount of photons received by the gamma camera and the position of the gamma camera.

The collimator of a conventional SPECT imaging system prevents the vast majority of photons emitted by the radiotracer from reaching the gamma camera. The sensitivity of the SPECT imaging system is therefore restricted by the collimator. Due to the reliance on collimators, SPECT conventionally exhibits poorer spatial resolution than positron emission tomography (PET). For at least this reason, PET is often preferred over SPECT, particularly for oncological and neurological imaging. However, SPECT imaging can be performed at a lower cost than PET imaging. Furthermore, there are a greater number of radiotracers that have been determined to be safe and suitable for SPECT imaging than PET imaging, such that SPECT can be used to investigate a greater number of physiological pathways than PET.

BRIEF DESCRIPTION OF THE DRAWINGS

FIGS. 2A to 2C illustrate examples of an array including four detectors acquiring fluxes of photons emitted from a source at three time points.

FIG. 3 illustrates an example environment including an attenuator having a shape of a rectangular prism.

FIG. 4 illustrates an example environment including an attenuator having a shape of a circular prism.

FIG. 8A illustrates an example environment of a single detector detecting a flux of photons emitted by a first source and a second source during an acquisition time. FIG. 8B illustrates a distribution of the flux detected by the detector during the acquisition time.

DETAILED DESCRIPTION

Figure 1B:
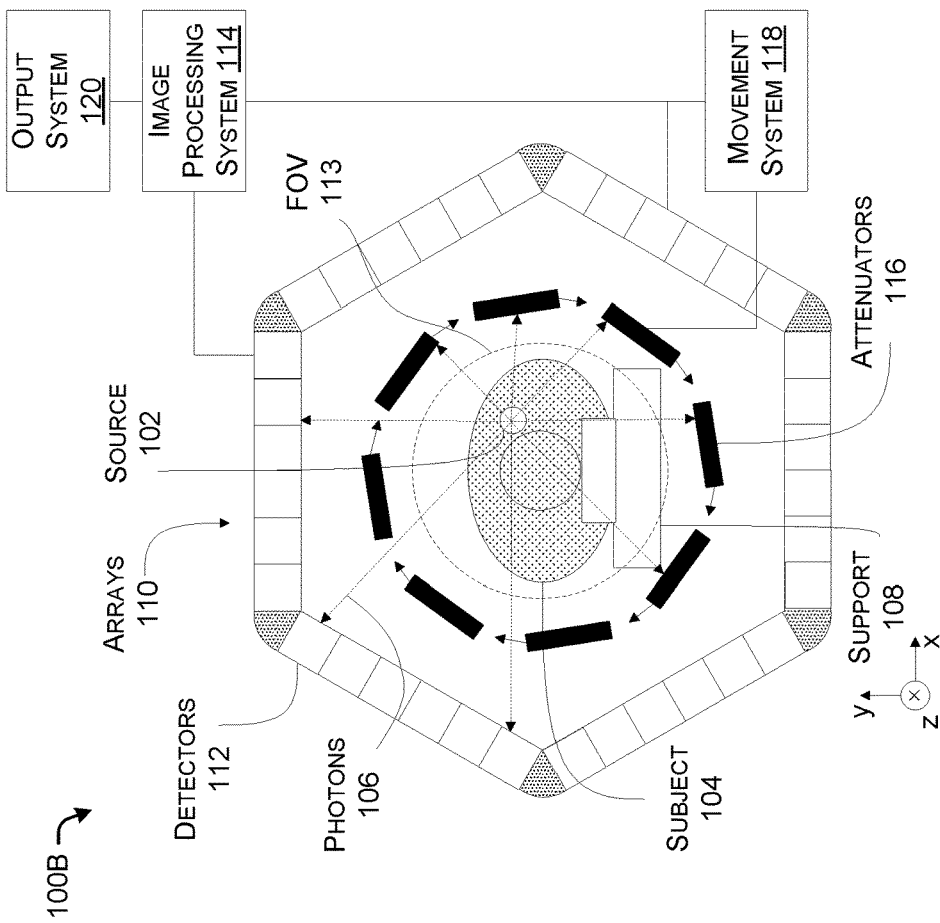
FIGS. 1A and 1B illustrate an example environment for performing SPECT imaging.

Various implementations described herein relate to high-resolution SPECT imaging systems, devices, and methods and solve multiple problems associated with existing SPECT imaging systems. In particular implementations, SPECT imaging can be performed without the use of a collimator, thereby providing significantly improved spatial resolution of acquired images, significantly reduced acquisition times, and/or significantly reduced radiation exposure for subjects being imaged. Accordingly, various SPECT imaging techniques described herein are suitable for high-resolution neurological and oncological imaging applications, among other uses.

The collimator in a conventional SPECT imaging system causes a number of significant problems. First, a conventional SPECT imaging system has relatively low detection efficiency to the injected activity because the collimator blocks the vast majority (e.g., 99.9%) of photons emitted by the radiotracer towards the gamma camera. Thus, the collimator significantly reduces the total number of photons that are detected by the gamma camera. Because of the low count statistics, filters are used to make the reconstructed images more visibly appealing; however, they also tend to smooth the image reducing image resolution. In conventional SPECT imaging systems, image resolution can be increased by increasing the acquisition time of a SPECT image allowing the images to be reconstructed will less filtering applied. For example, a SPECT imaging system may take 10-30 minutes to acquire a single SPECT image of a patient. However, such a lengthy acquisition time is inconvenient and uncomfortable for the patient, who remains still as the image is obtained. Another way that image resolution can be enhanced in a conventional SPECT imaging system is to increase the dose of radiotracer injected or disposed in the patient, which increases the number of photons that can be detected by the gamma camera. However, increasing the dose of the radiotracer also exposes the patient to a higher level of radiation.

Second, the collimator of a conventional SPECT imaging system creates a depth-based reduction in image resolution. A collimator restricts an angle at which a photon is received by the gamma camera, but a collimator cannot perfectly ensure that the photon is received perpendicularly to the gamma camera. As a result, the area where a source originating a photon can be located increases as the source is located a farther distance from the gamma camera.

Third, collimators in conventional SPECT imaging systems are unwieldy for users. In general, different types of collimators are appropriate for different types of radiotracers. Thus, if a user intends to use a high-energy radiotracer, the user may have to connect a collimator appropriate for the high-energy radiotracer to the conventional SPECT imaging system, but if the user intends to use a low-energy radiotracer, the user may have to connect a different collimator that is appropriate for the low-energy radiotracer. SPECT collimators are typically made of dense materials and can weigh hundreds of kilograms (kg), which can pose a significant challenge for safe movement during preparation and operation of a SPECT imaging system. When the SPECT imaging system is not in use, collimators are relatively large and take up a significant amount of storage space. Even when a particular collimator is fastened to the SPECT imaging system, many conventional imaging systems are configured to move the gamma camera in order to view the radiotracer and the patient at different angles. There are significant mechanical engineering challenges to designing and operating a SPECT imaging system that safely and reliably moves both the gamma camera and the heavy collimator during operation.

Various implementations of the present disclosure solve these and other problems associated with conventional SPECT imaging systems. In examples described herein, an imaging system can obtain high-resolution and high-sensitivity images of a radiotracer without a collimator. An example imaging system includes one or more detectors configured to detect a flux of photons emitted from a radiotracer, which may be disposed in a subject and/or may transmit photons through the subject. In some cases, a discrete attenuator is moved with respect to the subject during image acquisition. For example, the attenuator may be disposed at a distance from a sensing face of the detector(s). The attenuator absorbs photons emitted by the radiotracer and effectively casts a shadow on the detectors. In various examples, the shadow of the attenuator traverses the sensing face of the detector(s). Based on the flux (photons received per unit time, such as photons per second) detected by the detector(s) and the position of the attenuator over time, the example imaging system may generate an image of a field of view (FOV) of the detector(s).

In various implementations, by removing the collimator from the system and fully exposing the detector(s) to the source of photons, the detector(s) can measure total uncollimated counts from various regions within the FOV. This can provide a sufficient number of photon counts to estimate the LOR flux probability distribution; however, it may only yield the lowest-frequency information from the source. By including the attenuator, the photon flux to individual detectors can be manipulated. If the attenuator is moved in a specific trajectory during data acquisition, changes in flux to each detector element can be analyzed in a way that recovers the high-frequency information from the source.

In the absence of flux manipulation (e.g., a moving attenuator) and when the activity distribution is in steady state, the flux to each detector may be constant and the photon inter-arrival times are exponentially distributed: $t_{i+1} - t_i \sim \text{Exp}(\lambda)$, where t represents the photon detection times and $\lambda$ is the parameter of the exponential probability distribution (the reciprocal of the associated Poisson rate parameter $1/\lambda$). By strategically blocking the flux to each detector using the attenuator, the inter-arrival time parameter $\lambda$ can be continuously manipulated over the course of the acquisition and the data treated as an inhomogeneous point process. This is in contrast to counts-per-LOR binning and assuming a Poisson distribution. Careful design of the attenuator and its motion trajectory, together with tools of statistical point process theory, allow for the photon flux probability distribution for each detector to be estimated (rather than using measured LOR estimates, as in conventional SPECT imaging systems relying on collimation). Further, implementations described herein enable estimating numerous transaxial LOR flux rates and support fully 3D image reconstruction from a 4D flux dataset.

Implementations of the present disclosure are more similar to fully 3D PET data acquisition versus modern parallel hole collimator-based SPECT imaging, where the datasets are stacks of 2D Poisson-distributed histograms and transaxial LORs are generally not measured. The implementations described herein are vastly different from that used by parallel hole, pinhole aperture, and coded aperture-based SPECT cameras. Various implementations can generate high-resolution images without parallel-projection or list-mode reconstruction. In some cases, the direction of travel for individual photons is not considered. In various implementations, an image of a subject is generated based on the timestamps of photons as received by the detector(s), and by treating the data as an inhomogeneous point process to generate a probability distribution of the flux from various directions and/or angles to each detector. Furthermore, the spatial resolution versus sensitivity tradeoff for SPECT is not applicable to various implementations described herein and is replaced by a resolution versus acquisition time tradeoff. According to various implementations, the intrinsic spatial resolution can depend upon the speed of the attenuator and the number of translational passes over the face of the detector(s) during image acquisition.

According to example simulations, example noncollimated SPECT imaging systems produce hundreds (e.g., 100-300) of times the volumetric image resolution of collimated SPECT imaging systems (e.g., a standard low energy high resolution (LEHR) collimator-equipped gamma detector). Furthermore, example noncollimated SPECT imaging systems can achieve at least a thousand times detection efficiency to that of collimated SPECT imaging systems. In various implementations, an example noncollimated SPECT imaging system can support images with less than 2 millimeter (mm) image resolution throughout its FOV. For example, an example system may support less than 2 mm image resolution for Tc-90m human brain imaging. Accordingly, a noncollimated SPECT imaging system can produce images with significantly higher resolution than collimated SPECT imaging systems. In some cases, a noncollimated SPECT imaging system can obtain images with shorter acquisition times than collimated SPECT imaging systems. Further, in some examples, a noncollimated SPECT imaging system can produce images with a lower dose of radiotracer (and corresponding radiation to a subject) than collimated SPECT imaging systems. Additionally, the various techniques described herein can be used to produce a SPECT image with a resolution that has limited to no depth-dependency. Further, various implementations described herein can be operated without moving or storing a heavy collimator.

Particular examples will now be described with reference to the accompanying figures. The scope of this disclosure includes individual examples described herein as well as any combination of the examples, unless otherwise specified. Although various implementations are described herein with respect to SPECT imaging, implementations are not limited to SPECT imaging. For example, similar techniques can be adopted for PET, x-ray-based imaging, and other imaging modalities. Furthermore, specific elements of the figures are not necessarily drawn to scale.

Figure 1A:
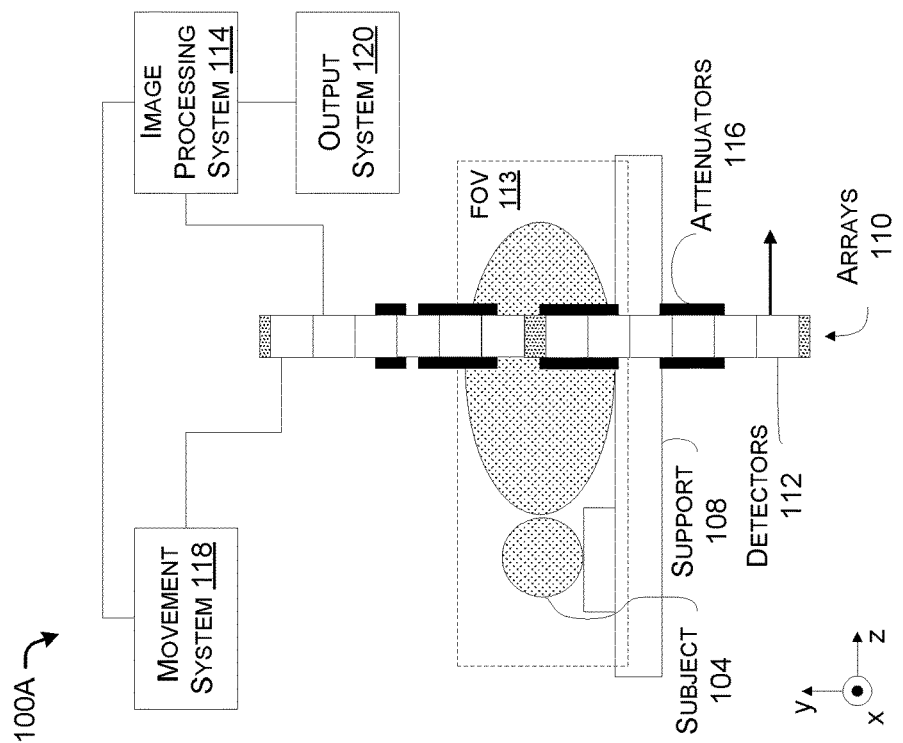

FIGS. 1A and 1B illustrate an example environment for performing SPECT imaging. FIG. 1A illustrates a first view of the environment 100A and FIG. 1B illustrates a second view of the environment 100B. As illustrated in FIG. 1B, a source 102 is disposed in a subject 104. In some cases, the subject 104 is a human, such as a patient. In some examples, the source 102 is injected into the subject 104, orally consumed by the subject 104, or otherwise disposed in the subject 104. In particular cases, the source 102 is disposed inside of a physiological structure of the subject 104. As used herein, the term "physiological structure," and its equivalents, can refer to at least one body part, an organ (e.g., the heart or the brain), one or more blood vessels, or any other portion of a subject. The physiological structure may be associated with a physiological function, which may be an expression of a particular ligand associated with the physiological structure. In some examples, the source 102 is configured to specifically bind to the ligand.

The source 102 is configured to emit photons 106. In some cases, the source 102 includes a radiotracer or some other substance configured to emit radiation. For instance, the source 102 may include at least one of technetium-99m, carbon-11, iodine-123, iodine-124, iodine-125, iodine-131, indium-111, copper-64, fluorine-18, thallium-201, rubidium-82, molybdenum-99, lutetium-177, radium-223; astatine-211; yttrium-90; gallium-67, gallium-68, or zirconium-89. In some cases, the source 102 is configured to bind to at least one biomolecule in the subject 104. In various examples, the photons 106 include at least one of x-rays or gamma rays. For instance, at least one of the photons 106 may have an energy of at least 124 electron volts (eV) and less than or equal to 8 MeV, a wavelength of at least 100 femtometers (fm) and less than or equal to 10 nanometers (nm), a frequency of at least 30 petahertz and less than or equal to 10 zettahertz, or any combination thereof. The photons 106 travel through at least a portion of the subject 104. In particular examples, the source 102 is disposed in a brain of the subject 104 and the photons 106 travel through a skull of the subject 104.

The subject 104 is disposed on a horizontal or substantially horizontal support 108, such as a bed, stretcher, chair, or padded substrate. In various examples, the photons 106 travel through the support 108, such that the support 108 includes a material that is transparent or is otherwise resistant to scattering or absorption of the photons 106. The support 108 is configured to support the subject 104, in various implementations. The subject 104 may be laying down or sitting on the support 108. For example, the support 108 may include a cushioned platform configured to support the weight of the subject 104 during image acquisition.

Arrays 110 of detectors 112 are configured to detect at least a portion of the photons 106. As shown in FIGS. 1A and 1B, the arrays 110 are disposed around the subject 104 and the support 108 in an annulus along an xy plane. In alternative implementations, one or more arrays 110 are moved around the subject 104 along the xy plane and configured to detect the photons 106 at different angles defined along the xy plane. In the perspective illustrated in FIG. 1A, the source 102 is obscured by the arrays 110.

The arrays 110 and/or detectors 112 are configured to detect photons 106 at least partially traversing a volumetric field-of-view (FOV) 113. The detectors 112, for example, include photosensors configured to detect the photons 116 that reach the detectors 112. The FOV 113 in FIGS. 1A and 1B is illustrated as a cylinder, however, implementations are not so limited. The FOV 113 includes various volumetric regions. In some examples, the regions of the FOV 113 respectively correspond to voxels of a volumetric image generated based on the photons 106 detected by the arrays 110 and detectors 112. In various implementations, the FOV 113 may be limited to a volumetric region that is projected from the edges of the arrays 110 along two xy planes that are parallel to the cross-section illustrated in FIG. 1B, and which intersect the edges of the arrays 110 defined along the z axis. For instance, shields (e.g., including a material configured to attenuate and/or reflect photons) may be disposed on the edges of the arrays 110 that prevent photons from outside of the limited volumetric region from reaching the arrays 110.

Each one of the arrays 110 includes multiple detectors 112. An example array 110 includes one or more rows of detectors 112 and one or more columns of detectors 112. For example, one of the arrays 110 includes row(s) extending in the x direction and column(s) extending in the z direction. In some cases, the row(s) and column(s) of an example array 110 extend in directions that are non-perpendicular to one another, such that an angle between the directions is greater than 0 degrees and less than 90 degrees. The detectors 112 are configured to detect the photons 106 that cross detection surfaces of the detectors 112. An example detector 112 includes a scintillation crystal (e.g., a sodium iodide crystal or GAGG) configured to receive a photon 106 at a detection surface and generate a lower-energy photon (e.g., an optical photon); as well as a sensor configured to generate an electrical signal based on the lower-energy photon generated by the scintillation crystal. In some instances, the detectors are pixelated into discrete detector elements and adjacent detectors 112 are separated by a barrier configured to prevent the lower-energy photons from traveling between crystals of the adjacent detectors 112. The barrier may include a material configured to reflect photons, such as $BaSO_4$; VIKUITI from 3M Corporation of Saint Paul, Minn.; LUMIRROR from Toray Industries, Inc. of Tokyo, Japan; $TiO_2$; or any combination thereof. An example detector 112 includes a semiconductor-based photomultiplier (e.g., a silicon photomultiplier) configured to generate an electrical signal based on a photon 106 received by the photomultiplier.

According to various implementations, each of the detectors 112 is configured to generate a signal based on the detected photon(s) 106 and to provide the signal to an image processing system 114. In some cases, the detectors 112 generate analog signals that are converted to digital signals by one or more analog to digital converters. The image processing system 114 is configured to generate the volumetric image of the FOV 113. In various examples, the image processing system 114 generates an image of the source 102 and/or the subject 104 based on the signals generated by the detectors 112. The image processing system 114 is implemented in hardware and/or software, for instance.

In various implementations, the arrays 110 and detectors 112 are noncollimated. As used herein, the term "noncollimated," and its equivalents, may refer to a system that omits or otherwise does not utilize a collimator. As used herein, the term "collimator," and its equivalents, refers to an object including one or more apertures, wherein the object is configured to attenuate photons that contact the object and to pass other photons transmitted through the aperture(s). Thus, the collimator selectively passes photons that are traveling in paths that extend through the aperture(s). As used herein, an aperture can be an opening in a material specifically designed and created to allow passage of photons approaching from a defined direction. Depending on the narrowness of the aperture(s), the collimator selectively passes photons with substantially predictable directions. For instance, a parallel hole collimator of a conventional SPECT system may selectively pass photons that are within 90±0.5 degrees of a detection surface of a gamma camera. Referring to FIGS. 1A and 1B, a collimator is absent from a space defined between the arrays 110 and the source 102.

Because the arrays 110 and/or detectors 112 are noncollimated, the detectors 112 receive a substantial portion of the photons 106 emitted from the source 102. However, the photons 106 are received at the detectors 112 at a variety of angles. For instance, an example detector 112 receives one or more of the photons 106 at an angle that is greater than 0 degrees and less than 85 degrees, 86 degrees, 87 degrees, 88 degrees, 89 degrees, 89.5 degrees, or 89.9 degrees. In some cases, the example detector 112 receives at least two of the photons 106, wherein an angle between the paths of the at least two photons 106 is between 10 and 170 degrees. For instance, the angle between the photons 106 received by the example detector 122 may be 10 degrees, 30 degrees, 40 degrees, 50 degrees, 60 degrees, 70 degrees, 90 degrees, 110 degrees, 130 degrees, 150 degrees, or 170 degrees.

In various implementations, attenuators 116 are disposed between the source 102 and the arrays 110 of detectors 112. The attenuators 116 include one or more materials configured to absorb at least a portion of the photons 106, such as tungsten, gold, platinum, uranium, lead and/or one or more alloys thereof. The attenuators 116, in various cases, are nonporous. Unlike a collimator, the attenuators 116 lack apertures in some examples. The attenuators 116 can be any of a variety of shapes, such as rectangular prisms, circular prisms, spheres, or the like. The attenuators 116 are spaced apart from each other by one or more distances. Although FIGS. 1A and 1B illustrate multiple attenuators 116, in some implementations, an example system may include a single attenuator 116.

The attenuators 116 are configured to move with respect to the source 102 and/or the detectors 112. For example, the attenuators 116 move along the xy plane. In various implementations, at least one of the attenuators 116 are translated in a direction that is at least partially parallel to a detection surface of at least one of the detectors 112. Accordingly, an attenuator 116 may cast a shadow on at least one of the arrays 110 and based on the photons 106 emitted from the source 102, wherein the shadow is translated along the detection surface(s) of the at least one array 110. In some examples, the attenuators 116 are moved rotationally about an axis that extends along the z direction.

In various examples, a movement system 118 is configured to move the attenuators 116. For example, the movement system 118 includes one or more actuators and/or motors configured to change a position of each one of the detectors 112. In some cases, the movement system 118 is further configured to move the arrays 110, such as in a direction that is different than the direction of movement of the attenuators 116 and/or at a different rate than the movement of the attenuators 116. In some examples, the movement system 118 outputs a signal to the image processing system 114 that indicates the position and/or movement of the attenuators 116.

As the attenuators 116 block at least a portion of the photons 106 emitted by the source 102, the flux of the photons 106 received by individual detectors 112 changes. As used herein, the term "flux," and its equivalents, can refer to the rate at which photons are received with respect to time. In a discrete environment, a flux of photons can be represented by the number of photons received during a discrete time interval. The image processing system 114 may determine the flux of photons 106 received by individual detectors 112 over time as the attenuators 116 are moved. For instance, the image processing system 114 may determine the number of the photons 106 received by an example detector 112 during each one of multiple time intervals, wherein the attenuators 116 are located at different positions during the time intervals.

In various implementations, the image processing system 114 is configured to identify a location of the source 102 based on the fluxes of the photons 106 received by the detectors 112. The attenuators 116, by moving along the xy plane, selectively block potential lines of response (LORs) from the source 102 to the detectors 112. The LORs are assumed to be straight lines, in various cases. Based on the fluxes of the photons 106 received by the detectors 112, the image processing system 114 may determine which LORs, in fact, correspond to the position of the source 102. For example, if a potential LOR passes through a space between the attenuators 116 and intersects a particular detector 112 and the detector 112 detects an initial flux of the photons 106, but then the potential LOR is blocked by one of the attenuators 116 and the detector 112 detects less than the initial flux of the photons 106, then the image processing system 114 may infer that the source 102 is located along the potential LOR. In contrast, if the detector 112 detects the initial flux of the photons 106 when the attenuator 116 is blocking the potential LOR, then the image processing system 114 may infer that the source 102 is not located along the potential LOR. Because the arrays 110 detect the photons 106 at different angles around the source 102, the image processing system 114 can use the fluxes detected by the detectors 112 to identify what voxels, in the FOV, correspond to the location of the source 102. Accordingly, the image processing system 114 may generate a volumetric image of the source 102 and/or the physiological structure of the subject 104.

During image acquisition, an example detector 112 may detect a first flux at which an example attenuator 116 blocks LORs from the source 102 and a second flux at which the example attenuator 116 exposes the LORs from the source. The example attenuator 116 may move a distance such that an example detector 112 detects the flux when the attenuator 116 fully blocks the photons 106 from the source 102 and also detects the flux when the attenuator 116 fully exposes the source 102 to the photons 106. The movement of the example attenuator 116 may therefore depend on the spacing between adjacent attenuators 116, a length of the attenuator 116, the distance between the attenuator 116 and the detector 112, the distance between the attenuator 116 and the source 102, the FOV of the detectors 112 and/or the arrays 110, or a combination thereof. The example attenuator 116, for instance, may have a length that is greater than or equal to 1 cm and less than or equal to a length of one of the arrays 110, wherein the length of the example attenuator 116 is parallel to the length of the array 110. In some examples, a distance between two adjacent attenuators 116 is greater than or equal to 10 mm and less than or equal to 10 cm.

In some cases, the image processing system 114 generates the volumetric image of the source 102, determines which regions in the FOV 113 correspond to the location of the source 102, and/or determines a distribution of the source 102 within the regions of the FOV 113 based on the locations of the attenuators 116. For example, the movement system 118 may indicate the locations and/or movements of the attenuators 116 to the image processing system 114.

In various implementations, the image processing system 114 records the time of interaction (e.g., a time of each photon 106 received) of each detector 112. Because the attenuators 116 may lower the photon flux to individual detectors 112 in a specifically defined pattern over time, the image processing system 114 may generate a probability distribution of a flux-per-LOR of each of the detectors 112. In some cases, the flux-per-LOR data is defined as a sinogram for the purposes of image reconstruction. For example, various methods of image reconstruction, such as filtered backprojection (FBP) and/or maximum likelihood estimation method (MLEM), can be used to generate a tomographic image of the FOV 113 using the flux-per-LOR data rather than photon counts for image reconstruction.

In some examples, an example attenuator 116 is raster-scanned across the face of an example detector 112, wherein the example attenuator 116 is disposed at some distance from the sensing face of the example detector 112. A "fully-exposed flux" of the example detector 112 is measured when example attenuator 116 is not disposed between the LORs extending between the source 102 and the example detector 112. As the example attenuator 116 moves, LORs from the source 102 to the example detector 112 are selectively attenuated by the example attenuator 116 and the flux detected by the example detector 112 is lower than the fully-exposed flux when the example attenuator 116 blocks the LORs from the source 102 at various moments in time. Notably, the example attenuator 116 blocks different detectors 112 from the source 102 to different extents (e.g., at different angles) while at any example position, ensuring that the example attenuator 116 may manipulate the flux of multiple detectors 112. For the example detector 112 at each moment in time, the amount of flux lost from the fully exposed flux rate is equal to the amount of flux from the LORs blocked by the example attenuator 116. Accordingly, the flux from every line of response emanating from the example detector 112 to various regions within the FOV 113 can be determined and a 4-dimensional flux line-of-response dataset can be determined. This flux information can then be reconstructed using fully 3D image reconstruction techniques.

In some implementations, the LORs for the example detector 112 blocked in any time-interval represent a strip (a "fan-beam") through the FOV 113 that corresponds to the example attenuator 116. Therefore, the time-derivative of the flux detected by the example detector 112 corresponds to the line-integrals through the FOV 113 as perceived by the example detector 112.

The movement system 118 may move the example attenuator 116 and the image processing system 114 may detect various line integrals through the flux perceived by the example detector 112. This data can be reconstructed via standard methods for inverting the radon, fan beam, or X-ray transform including Fourier methods or statistically based reconstruction methods. This means that for the example detector 112, a 2D image reconstruction problem is solved and the solution yields the flux distribution seen by the example detector 112 (a distribution of flux-per-LOR for the example detector 112). This process can be repeated for each detector 112, and the image processing system 114 can use this data to tomographically reconstruct an image of the FOV 113 to estimate the 3D distribution of the source 102.

For example, the image of the FOV 113 can be generated based on the following method: (1) identify photons 106 detected by the detectors 112 and the times at which the photons 106 are detected by the detectors 112; (2) for each detector 112, estimate the photon flux as a function of time; (3) compare the photon flux measured to the flux loss anticipated by the movement of the attenuator 116 (e.g., using a finite number of timepoints within an acquisition time interval and/or continuously across the acquisition time); (4) use the comparison from (3) to generate a distribution of flux-per-LOR for each detector 112, wherein each detector is associated with multiple LORs respectively extending from regions of the FOV 113, and the distribution of flux-per-LOR can be generated by taking the derivative of the flux detected by each detector 112 with respect to time in order to obtain differential flux rates for each detector 112 (e.g., radon inversion, although X-ray, fan beam or another inversion can be used); (5) arrange the LOR-flux data from (4) into a tomographic dataset (e.g., a sinogram or similar structure); and (6) reconstruct the image of the FOV 113 using one or more image reconstruction algorithms (FBP, MLEM, etc.) on the tomographic dataset.

In some implementations, the image processing system 114 generates the image of the FOV 113 by modeling the motion of the attenuators 116 directly in the following Equation 1:

$$Pf=g \qquad \text{Equation 1}$$

wherein P represents the physical effects of the attenuators 116 on the detectors 112 at different points in time, f is the pixelized or voxelized FOV 113 to be reconstructed, and g is a vector representing the fluxes detected by the detectors 112 at the different points in time. In various implementations, P represents the impact of the position of the attenuators 116 on the detectors 112 with respect to photon 106 transport, geometric sensitivity, attenuation, scatter, or any other time-varying impact of the attenuators 116 on photon flux detected by the detectors 112. Equation 1 is invertible, meaning that f can be reconstructed exactly.

Preliminary simulations indicate that the inversion is robust when faced with imaging noise, as represented by the following Equation 2:

$$Pf=g+e \qquad \text{Equation 2}$$

wherein e represents noise that corrupts the fluxes of g.

The system matrix, P, can be generated by considering the "rows" (the range-space) of the system matrix (the imaging operator) to include the Cartesian Product or other combination of space and time of the set of detectors 112 with respect to time. Time can be considered as either a discrete or continuous space in this consideration. Each column of the system matrix can be represented by the pixels or voxels that make up the image of the FOV 113.

In conventional image reconstruction methods, the sensitivity of an individual detector to a given pixel or voxel is fixed over time. In various implementations described herein, by detecting photon fluxes of the detectors 112 over time, rather than a sum of total counts, the image processing system 114 may treat image reconstruction as an inhomogeneous point process and instantaneous flux can be computed in a variety of different ways, allowing the flux to be estimated as a function of time over the course of image acquisition.

For example, the image of the FOV 113 can be reconstructed using Equation 1 by performing the following steps: (1) create a system matrix (the imaging operator), P, by labeling matrix rows (discrete or continuous) as location-time pairs (the Cartesian product or other combination of detector positions and time) and columns as regions of the FOV 113 corresponding to pixels or voxels in the image, wherein the elements of P are the sensitivities of the detectors 112 to the regions of the FOV 113 at various times in the image acquisition time interval; (2) record photons detected by the detectors 112 and time-of-detection (e.g., timestamp) pairs to compute flux for each detector 112 as a function of time and arrange this flux data into a data array, g, that matches the row-labels from (1); (3) solve Equation 1 for the image f using any standard method for solving linear equations.

The incorporation of time into the rows P is at least one novel feature of Equation 1. In traditional imaging operators, the rows are spatially defined (e.g., LORs) and the columns are also spatially defined (e.g., regions in the FOV 113 corresponding to pixels or voxels). In various implementations herein, the rows of P are a Cartesian Product or other combination of space and time.

According to various implementations, the image processing system 114 uses the locations and/or movements of the attenuators 116 to identify sensitivities of an example detector 112 to photons 106 transmitted from each of the regions in the FOV 113 due to the positions of the attenuators 116. A sensitivity may be a number that is greater than or equal to 0 and less than or equal to 1. For example, if the attenuator 116 is disposed between a particular region in the FOV 113 and the example detector 112, the example detector 112 may have a relatively low sensitivity (e.g., 0.5) to photons 106 from that region, whereas the example detector 112 may have a relatively high sensitivity (e.g., 0.95) to photons 106 from a region exposed by the attenuators 116. The image processing system 114 can generate the volumetric image of the FOV 113, wherein each sub-region corresponds to a respective voxel of the volumetric image.

In some implementations, the image processing system 114 can determine the location of the source 102 based on the shapes of the attenuators 116, which can be used to predict the shadows projected onto the detectors 112 from the FOV 113. According to some implementations, the image processing system 114 may use deep learning techniques to infer the location of the source 102 based on the fluxes detected by the detectors 112. For example, the image processing system 114 may store a convolutional neural network (CNN). The image processing system 114 may train the CNN by optimizing various parameters of the CNN based on known images of the FOV 113 and the fluxes detected by the detectors 112 while the known images of the FOV 113 are obtained. Once the CNN is trained, the image processing 114 may utilize the trained CNN to identify a new image of the FOV 113 based on fluxes detected by the detectors 112 during a new acquisition time.

To improve resolution of the volumetric image of the FOV 113, the movement system 118 may be further configured to translate the arrays 110 and the attenuators 116 along the z direction while the image processing system 114 determines the fluxes detected by the detectors 112. For instance, the movement system 118 may scan the arrays 110 and attenuators 116 down a length of the subject 104. Thus, even in examples in which the arrays 110 are configured to receive the photons 106 from the limited volumetric region that is defined between two xy planes intersecting the edges of the arrays 110 and parallel to the cross-section illustrated in FIG. 1B, the arrays 110 may capture photons from the entire width of the FOV 113 defined in the z direction based on repositioning the arrays along the z direction.

In examples in which the detectors 112 have a finite sampling resolution for photon flux over time, the resolution of the image generated by the image processing system 114 may be correlated to the speed at which the attenuators 116 are moved. In some examples, the movement system 118 may move the attenuators 116 at different speeds in order to obtain a volumetric image of the FOV 113 with different levels of resolution. In some cases, a user may specify one or more region within the FOV 113 of the arrays 110 (e.g., using an input device communicatively coupled to the image processing system 114 and/or the movement system 118), the movement system 118 may move the attenuators 116 at a relatively slow speed when the attenuators 116 are disposed between the specified region(s) and the arrays 110, and the movement system 118 may move the attenuators 116 at a relatively high speed when the attenuators 116 are located at other positions. In some cases, the movement system 118 may move the arrays 110 and the attenuators 116 in the z direction at a relatively slow speed when the attenuators 116 are disposed between the arrays 110 and the specified region(s). An example of the specified region could be, for instance, the heart or brain of the subject 104. In some cases, the image processing system 114 may increase the acquisition time for fluxes detected by the detectors 112 when the fluxes are indicative of the specified region(s), because the image resolution is positively correlated to the acquisition time.

Although not illustrated in FIGS. 1A and 1B, in some cases, the image processing system 114 may further receive data indicative of a volumetric image of the subject 104 using a different imaging modality. For instance, an x-ray computed tomography (CT) imaging system, an ultrasound imaging system, or a magnetic resonance imaging (MRI) system may be configured to generate the data. The image processing system 114 may generate the image of the FOV 113 further based on the data indicative of the other volumetric image of the subject 104. For example, if the image processing system 114 estimates that the source 102 is disposed in a sub-region of the FOV 113 that the other volumetric image indicates includes a bone of the subject 104, and the source 102 is known to be outside of the bone of the subject 104 (e.g., the source 102 is a radiotracer configured to flow through the vasculature of the subject 104), then the image processing system 114 can correct the location of the source 102 within the FOV 113 in the volumetric image of the FOV 113 based on the other volumetric image of the subject 104.

An output system 120 may be configured to output the position and/or the image of the source 102. In various examples, the output system 120 includes a display configured to visually output the volumetric image of the FOV 113. A user may view the position and/or image of the source 102 in order to diagnose a condition of the subject 104. For example, the display may be configured to output one or more two-dimensional images corresponding to slices of the volumetric image of the FOV 113. In some examples, the display is configured to output a perspective view of the volumetric image of the FOV 113. In some cases, the output system 120 is configured to output a location of the source 102 within the FOV 113.

FIGS. 2A to 2C illustrate examples of an array 202 including four detectors 204 acquiring fluxes of photons 206 emitted from a source 208 at three time points. FIG. 2A illustrates first fluxes received by the detectors 204 when an attenuator 210 is located at a first position. FIG. 2B illustrates second fluxes received by the detectors 204 when the attenuator 210 is located at a second position. FIG. 2C illustrates third fluxes received by the detectors 204 when the attenuator 210 is located at a third position. Based on the fluxes, an imaging system may infer that the source 208 is located in region $r_2$ rather than region $r_1$ or $r_3$.

In FIG. 2A, a lagging edge of the attenuator 210 is at $x_{a1}$ and a leading edge of the attenuator 210 is positioned at $x_{a2}$. A proximate edge of the attenuator 210 is at $y_1$ and a distal edge of the attenuator 210 is at $y_2$. For the sake of simplicity, a detection face of the detectors 204 may be defined at y=0. Among the detectors 204, A is blocked from receiving photons 206 from the source 208, whereas B, C, and D receive photons 206 from the source 208. Thus, at the first time, a flux detected by A $a_1$ is smaller than a flux detected by B $b_1$, a flux detected by C and a flux detected by D $d_1$.

In FIG. 2B, the lagging edge of the attenuator 210 is at $x_{a2}$, a leading edge of the attenuator 210 is at $x_{b2}$, wherein $x_{a2} > x_{a1}$ and $x_{b2} > x_{b1}$. Among the detectors, A, B, and C are blocked from receiving photons 206 from the source 208, whereas D receives photons 206 from the source 208. Thus, at the second time, a flux detected by A ($a_2$), a flux detected by B ($b_2$), and a flux detected by C ($c_2$) are less than a flux detected by D ($d_2$).

In FIG. 2C, the lagging edge of the attenuator 210 is at $x_{a3}$, a leading edge of the attenuator 210 is at $x_{b3}$, wherein $x_{a3} > x_{a2}$ and $x_{b3} > x_{b2}$. Among the detectors, A and B receive photons 206 from the source 208, whereas C and D are blocked from receiving photons 206 from the source 208. Thus, at the third time, a flux detected by A ($a_3$) and a flux detected by B ($b_3$) are greater than a flux detected by C ($c_3$) and a flux detected by D ($d_4$).

In various implementations, the imaging system generates an image of an FOV including regions $r_1$, $r_2$, and $r_3$ based on the fluxes detected by the detectors 204 at the first, second, and third times. For example, the image may include three pixels $p_1$, $p_2$, and $p_3$ corresponding respectively to $r_1$, $r_2$, and $r_3$. In various implementations, a 2D image includes multiple pixels. As used herein, the term "pixel," and its equivalents, may refer to a portion of an image that corresponds to a one- or two-dimensional region of an FOV and which is assigned a value corresponding to an amount and/or type of photons transmitted from the region of the FOV. In some examples, the image is a grayscale image and the value of the pixel is greater than or equal to 0 and less than or equal to 255. In some cases, the image is a color image (e.g., a red-green-blue (RGB) image) and includes multiple values corresponding respectively to multiple color channels, wherein the value of a particular color channel corresponds to the amount of photon having a particular color (e.g., a frequency range) that are emitted from the region. As used herein, the term "voxel," and its equivalents, may refer to a portion of an image that corresponds to a three-dimensional region of the FOV and is assigned a value corresponding to an amount and/or type of photons transmitted from the region of the FOV.

Returning back to FIGS. 2A to 2C, the values of the pixels $p_1$, $p_2$, and $p_3$ may respectively correspond to the magnitude of photons emitted from $r_1$, $r_2$, and $r_3$. In the simplified example of FIGS. 2A to 2C, the image may be a one-dimensional image with three pixels, wherein pixel $p_2$ has a nonzero value and pixels $p_1$ and $p_3$ have zero values, because the source 208 is located in $r_2$ without occupying $r_1$ or $r_3$. Alternatively, pixel $p_2$ may have zero values and pixels $p_1$ and $p_3$ have nonzero values, due to the position of the source 208 in $r_2$.

In some cases, the imaging system generates the image of the FOV by comparing potential LORs from $r_1$, $r_2$, and $r_3$ to the fluxes detected by the detectors 204. For example, at the first time, because $a_1 < b_1$, $c_1$, or $d_1$, the imaging system may infer that the attenuator 210 is disposed between the source 208 and A, but is not disposed between the source 208 and B, C, or D. As a result, the imaging system may determine that the source 208 is not located in $r_3$, which remains exposed to A by the attenuator 210 at the first time. However, the imaging system may be unable to determine whether the source 208 is located in $r_1$ and/or $r_2$ based on the fluxes detected at the first time, alone. At the second time, because $a_2$, $b_2$, and $c_2 < d_2$, the imaging system may infer that the attenuator 210 is disposed between the source 208 and A, B, and C, but is not disposed between the source 208 and D. However, because A remains exposed to $r_1$ by the attenuator 210 at the second time, the imaging system may conclude that the source 208 is not located in $r_1$. Because the source 208 is not located in $r_1$ or $r_3$, the imaging system may assign zero pixel values to $p_1$ and $p_3$. Further, because the imaging system has determined that the source 208 is located in $r_2$, the imaging system may assign a nonzero pixel value to $p_2$.

According to some implementations, the imaging system may generate the image of the FOV using a matrix-based technique. For example, the imaging system may generate a vector g that includes the fluxes detected by the detectors 204 at the first through third times. Vector g may have a single column, wherein its first (three) values correspond to the fluxes detected by A at the first through third times, the next (three) values correspond to the fluxes detected by A at the first through third times, and so on. For instance, vector g may be defined as follows:

$$g = [a_1\ a_2\ a_3\ b_1\ b_2\ b_3\ c_1\ c_2\ c_3\ d_1\ d_2\ d_3]^T \qquad \text{Equation 3}$$

In addition, the imaging system may generate a matrix P that includes the sensitivities of the detectors 204 to photons from the three regions $r_1$, $r_2$, and $r_3$ at the first through third times. An example row of P has three elements corresponding to the sensitivities of a particular detector 204 at a particular time to regions $r_1$, $r_2$, and $r_3$. For example, if a detector u has a sensitivity of $S_{u,v,w}$ to a given region v at time w, P could be defined as follows:

$$P = \begin{bmatrix} s_{a,1,1} & s_{a,1,2} & s_{a,1,3} & s_{b,1,1} & s_{b,1,2} & s_{b,1,3} & s_{c,1,1} & s_{c,1,2} & s_{c,1,3} \\ s_{a,2,1} & s_{a,2,2} & s_{a,2,3} & s_{b,2,1} & s_{b,2,2} & s_{b,2,3} & s_{c,2,1} & s_{c,2,2} & s_{c,3,1} \\ s_{a,3,1} & s_{a,3,2} & s_{a,3,3} & s_{b,3,1} & s_{b,3,2} & s_{b,3,3} & s_{c,3,1} & s_{c,3,2} & s_{c,3,3} \end{bmatrix}^T \quad \text{Equation 4}$$

For example, the sensitivity of A at the first time to photons from region $r_3$ can is $s_{a,3,1}$; the sensitivity of B at the second time to photons from region $r_1$ is $s_{b,1,2}$, and so on. In some cases, each one of the sensitivities in P is greater than or equal to 0 and less than or equal to 1. In the example of FIGS. 2A and 2B, $s_{a,3,1}$ may be nonzero (e.g., 1) because A is exposed to $r_3$ at the first time, and $s_{b,1,2}$ may be zero or at least smaller than $s_{a,3,1}$ because the actuator 210 is disposed between B and $r_1$. The elements of P may be generated based on the position of the attenuator 210 at the different times, as well as the relative geometry between the detectors 204, the attenuator 210, and $r_1$, $r_2$, and $r_3$. In some cases, the attenuator 210 blocks an incomplete amount of photons 206 along a particular LOR. The amount of photons 206 blocked by the attenuator 210 may correspond to the thickness of the attenuator 210 along the potential paths (e.g., LORs) of the photons 206. For example, an example element of P corresponding to a sensitivity of a particular detector 204 to a particular region at a particular time may be negatively correlated to a length of a path of one or more LORs from the region to the particular detector 204 that traverses through the attenuator 210. For instance, the sensitivity of A at the second time to $r_2$ may be lower than the sensitivity of C at the second time to $r_2$, since any photons 206 emitted by the source 208 and traversing the attenuator 210 would have to traverse a longer section of the attenuator 210 to arrive at A than at B. The imaging system may solve for a vector f representing the pixels $p_1$, $p_2$, and $p_3$ by solving Equation 1, wherein f is defined as the values of pixels $p_1$, $p_2$, and $p_3$. In other words, f can be defined as follows:

$$f=[p_1 p_2 p_3]^T \qquad \text{Equation 5}$$

In some examples, the values of vector f are further normalized to a range between 0 to 255, wherein the lowest value of f is set to 0 and a highest value of f is set to 255, and the values of f correspond to grayscale pixels of the image of the FOV. In the example of FIGS. 2A to 2C, $p_1$ and $p_3$ may be equal to zero, because none of the photons 208 are transmitted from $r_1$ or $r_3$, and $p_2$ may be nonzero (e.g., normalized to 255), because all of the photons 208 are transmitted from $r_2$.

Although Equation 1 is described with reference to the simplified example of FIGS. 2A to 2C, Equation 1 is generalizable to more complex environments. For example, Equation 1 can be used to solve for numerous (e.g., thousands of, millions of, or the like) pixels of a two-dimensional image and/or numerous (e.g., thousands of, millions of, or the like) voxels of a volumetric image.

In some examples, the imaging system may generate the image of the FOV based on the derivative of the fluxes of the photons 106 detected by the detectors 204 over time. For instance, the flux detected by A over time may be determined. In a plot of the flux detected by A over time, the flux may decrease at the time at which the LORs from the source 208 to A are blocked by the attenuator 210. In addition, the flux may increase at the time when the LORs from the source 208 to A are exposed by the attenuator 210. Thus, the minimum of the derivative of the flux with respect to time may correspond to the time at which the attenuator 210 transitions from exposing to blocking the source 208 from A, and the maximum of the derivative of the flux with respect to time may correspond to the time at which the attenuator 210 transitions from blocking to exposing the source 208 to A. According to various implementations, the imaging system may calculate the time derivative of the flux of each detector 204 over time and use each derivative as a sinogram. The imaging system may then use existing image reconstruction techniques on each sinogram to generate the image of the FOV. Thus, in various implementations, the imaging system may generate the image of the FOV based on the derivatives of the fluxes detected by the detectors 204 with respect to time.

FIG. 3 illustrates an example environment 300 including an attenuator 302 having a shape of a rectangular prism. In various implementations, an array 304 extends in a first direction (e.g., an x direction) and a second direction crossing the first direction (e.g., a z direction). The array 304 may include a detector 306. In various implementations, the array 304 includes at least one row of detectors extending in the first direction and at least one row of detectors extending in the second direction. The attenuator 302 is spaced apart from the array 304 in a third direction (e.g., a y direction) crossing the first and second directions.

In various implementations, the attenuator 302 is translated across the array 304 in the first direction and/or second direction. As the attenuator 302 is moved, the attenuator 302 selectively blocks LORs 308 extending from the detector 306. The LORs 308, in some cases, extend between the detector 306 and regions of an FOV of the array 304. When the attenuator 302 blocks an example LOR 308, the sensitivity of the detector 306 to the LOR 308 (and the corresponding region of the FOV from which the LOR 308 extends) decreases. If a source of photons is located along the blocked LOR 308, the flux of photons detected by the detector 306 will decrease. During image acquisition, the attenuator 302 will move between a first position at which the detector 306 is fully exposed to the LORs 308 and a second position at which the LORs 308 are blocked. The detector 306 may detect a first flux of photons when the attenuator 302 is at the first position and a second flux of photons when the attenuator 304 is at the second position, wherein the first flux is greater than the second flux, and the second flux is below a particular threshold. In some cases, the second flux is zero, and in other cases, the second flux is nonzero and representative of minimal scatter of photons to the detector 306 from outside of the LORs 308.

When the attenuator 302 is located at a particular position, the detector 306 will detect photons transmitted along the LORs 308 from regions within the FOV of the detector 306. Because the detector 306 is not equipped with a collimator, the LORs 308 for the individual photons are not restricted. However, when the attenuator 302 blocks a particular LOR 308 the sensor signal (e.g., the flux detected by the detector 306) is reduced for that LOR 308. The reduction in the sensor signal for the blocked LOR 308 therefore provides information about the amount of the detected signal that was due to the blocked LOR 308. In a simplified analysis, the difference between the sensor signal from a particular LOR 308 before it was blocked by the attenuator 302 less the sensor signal when LOR 308 is blocked, may represent the sensor signal attributable to the blocked LOR 308. For example, the imaging may be conducted under quasi-steady state conditions, wherein the activity is changing over the course of the data acquisition, but the attenuator 302 is translating relatively quickly such that the imaged FOV is substantially in a steady during the time period associated with a particular pass of the attenuator 302. In other embodiments a dynamic imaging process may be used, wherein the photon emissions change during the data acquisition period, and multiple passes of the attenuator 302 may be needed associated with different rotation angles.

By raster-scanning the attenuator 302 over the face of the array 304, the flux from all LORs from every detector in the array 304 can be computed. The amount of flux per LOR for each detector in the array 304 can be used to produce a reconstructable dataset for image generation. The reconstructable dataset can be used to determine the distribution of the source of the photons within the FOV.

FIG. 4 illustrates an example environment 400 including an attenuator 402 having a shape of a circular prism. In various implementations, the attenuator 402 is spaced apart from the array 302 in the third direction (the z direction). The attenuator 402 may be translated across the array 304 in the first direction and/or the second direction. As the attenuator 402 is moved, the attenuator 402 selectively blocks LORs 308 extending from the detector 306. Thus, an image of the FOV can be generated based on the photon flux detected by the detector 306 as the attenuator 402 is moved.

During image acquisition, the attenuator 402 will move between a third position at which the detector 306 is fully exposed to the LORs 308 and a fourth position at which the LORs 308 are blocked. The detector 306 may detect a third flux of photons when the attenuator 302 is at the third position and a fourth flux of photons when the attenuator 304 is at the fourth position, wherein the third flux is greater than the third flux, and the fourth flux is below a particular threshold. In some cases, the fourth flux is zero, and in other cases, the fourth flux is nonzero and representative of minimal scatter of photons to the detector 306 from outside of the LORs 308.

Although FIGS. 3 and 4 illustrate prism-shaped attenuators 302 and 402, implementations are not so limited. In some cases, an attenuator with the shape of a web, a sphere, a pyramid, or another type of three-dimensional shape, may be utilized. In various examples, the detector 306 receives photons from LORs 308 at a wide variety of angles (e.g., a range of 0 to180 degrees) with respect to a detection face of the detector 306.

Figure 5:
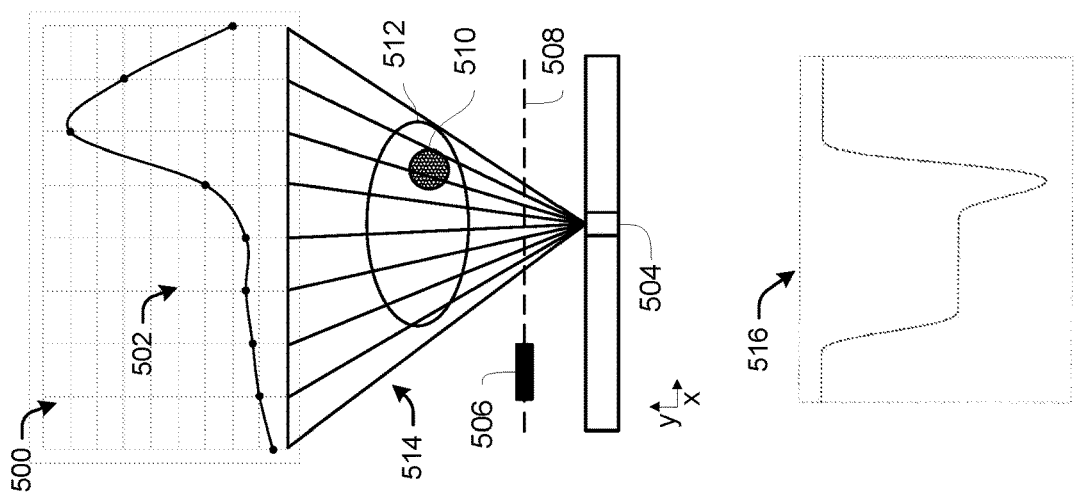
FIG. 5 illustrates an example environment of a probability distribution generated based on a photon flux detected by a detector within an array as an attenuator is moved along a path.

FIG. 5 illustrates an example environment 500 of a probability distribution 502 generated based on a photon flux detected by a detector 504 within an array as an attenuator 506 is moved along a path 508. In some cases, the probability distribution 502 can be replaced with a non-probabilistic distribution indicative of photon flux detected by the detector 504 with respect to the position and/or movement of the attenuator 506 along the path 508. In particular, the detector 504 detects a flux of photons emitted from a source 510 as the attenuator 506 is moved along the path 508 during an acquisition time. The detector 504 may be one of multiple detectors in an array 510. The source 510 may be disposed in a subject 512. In various implementations, the environment 500 represents a side view of the example environment 400 illustrated in FIG. 4, wherein the attenuator 402 is the attenuator 506. By translating the attenuator 506, multiple LORs 514 are obstructed simultaneously from each detector 504 in the array, selectively blocking an entire fan of LORs 514. The photon flux for the detector 504 may be reduced as the attenuator 506 passes and obstructs at least some of the LORs 514 from the detector 504.

When the attenuator 506 is not present, the detector 504 may be enabled to accept photons along all of the LORs 514 and thus the photon flux (the number of photons detected per second) of the detector 504 corresponds to an aggregated photon flux emitted from the entire FOV of the detector 504. As the attenuator 506 traverses its path 508, some LORs 514 will encounter reduced photon flux as the attenuator 506 obstructs incoming photons along the LORs 514 that intersect the attenuator 506. By knowing the position of the attenuator 506 and the position of the detector 504, the LORs 514 obstructed by the attenuator 506 can be calculated.

In various implementations, an imaging system may generate the probability distribution 502 based on the flux detected by the detector 504 and the position of the detector 504 throughout the acquisition time. The probability distribution 502 may represent the probability that photons received by the detector 504 are transmitted along the LORs 514. For example, if there are nine LORs 514, the probability distribution 502 may include nine probability values. The probability associated with a particular LOR 514 corresponds to an amount of an observed change in the flux detected by the detector 504 between a first time at which the attenuator 506 exposes the particular LOR 514 and a second time at which the attenuator 506 blocks the particular LOR 514. For example, the leftmost LOR 514 illustrated in FIG. 5 is associated with a relatively low probability, since the difference in flux detected by the detector 504 when the attenuator 506 blocks the leftmost LOR 514 versus when the attenuator 506 exposes the leftmost LOR 514 is relatively small, because the source 510 is not located along the leftmost LOR 514. However, an LOR 514 intersecting the source 510 is associated with a relatively high probability, since the difference in flux detected by the detector 504 when the attenuator 506 blocks the LOR 514 is relatively large. The imaging system may generate an image of the FOV based on the probability distribution 502.

The photon flux detected by the detector 504 as a function of the position of the attenuator 506 is shown as distribution 516. As the flux drops due to the leading edge of the attenuator 506 obstructing a set of the LORs 514, the amount of flux lost to this obstruction corresponds to the amount of flux contribution from those lines. Thus, the slope of the of the distribution 516 represents the value of the line integrals of flux through multiple LORs 514. The detector 504 responses across many such lines can be used to calculate the full LOR versus flux function for a single detector position. This could be achieved, for example, by translating the attenuator 506, rotating slightly, then translating back and repeating this motion until enough line integrals are measured to allow for the computation of individual LOR 514 flux measurements.

Once the flux for all of the LORs 514 are known, conventional imaging methods may be used to generate the image of the FOV using 2D or 3D image reconstruction. For example, multiple 3D data sets are collected (e.g., 4D—a data set similar to PET imaging systems). This mechanical flux manipulation described here is not limited to using the specific shape of the attenuator 506 illustrated in FIG. 5. The attenuator 506 may have a different shape or even a combination of different shapes to mechanically manipulate the photon flux detected by the detector 504. In some cases, the attenuator 506 may have cross-sectional shapes that are squares, cones, triangles, annuli, circles with varying thickness, or any other shape that has favorable flux-manipulation properties. In some examples, the attenuator 506 may include a rod or grid-like object of variable width or variable thickness, arrays of rods (or grids) that move in sequence or in tandem, multiple rods (or grids) with different thickness or width, circular or other cross-section rods (or grids), rods with curved edges, or moving slats. Furthermore, in some examples, the attenuator 506 need not be raster scanned, but could move along curved trajectories, along space-filling curves, or at variable speeds to achieve the desired mechanical flux manipulation.

Figure 6B:
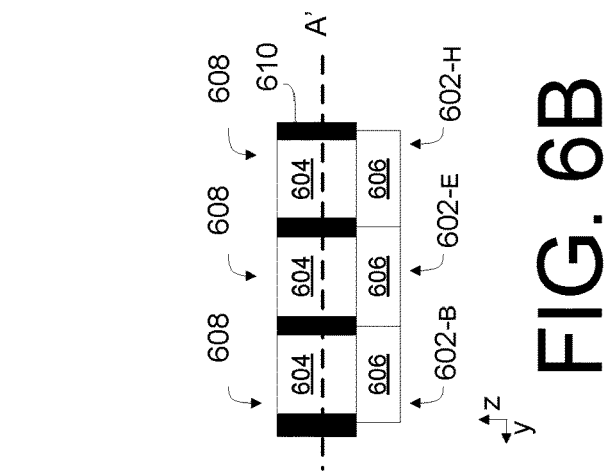
FIGS. 6A and 6B illustrate an example of a 3 by 3 detector array.
Figure 6A:
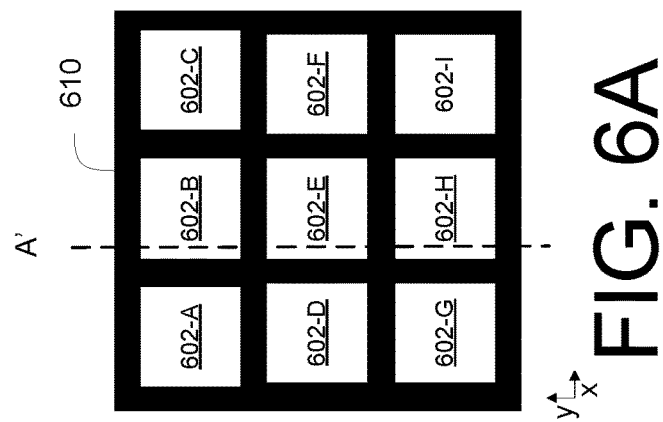

FIGS. 6A and 6B illustrate an example of a 3 by 3 detector array 600. FIG. 6A illustrates a top view of the detector array 600 and FIG. 6B illustrates a cross-sectional view of the detector array 600. The line A' is illustrated in both FIGS. 6A and 6B. In various implementations, the detector array 600 includes first through ninth detectors 602-A to 602-I. The detectors 602-A to 602-I are arranged in three rows extending in an x direction and three columns extending in a y direction.

Each of the detectors 602-A to 602-I includes a crystal 604 and a sensor 606. The crystal 604 includes a sensing face 608, at which photons are received. The crystal 604 may be configured to generate relatively low-energy photons (e.g., visible light) based on receiving relatively high-energy photons (e.g., x-rays or gamma rays) from the FOV of the detector array 600. The low-energy photons may be sensed by the corresponding sensor 606.

To avoid the relatively low-energy photons from traveling between the crystals 604, a barrier 610 may be disposed between the crystals 604. The barrier 610 may include a material configured to reflect the relatively low-energy photons. Accordingly, the low-energy photons received by the sensor 606 of a particular detector 602 may correspond to a high-energy photon received by the crystal 604 of the particular detector 602.

Figure 7B:
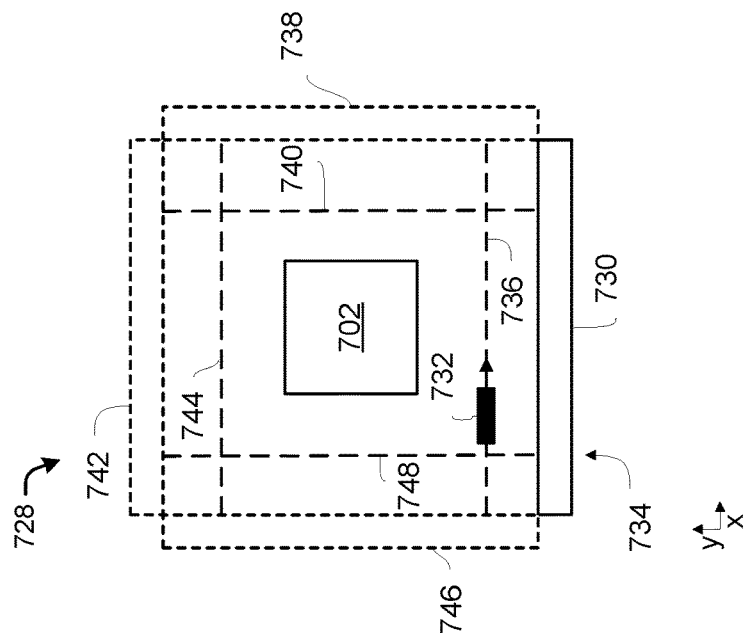
FIG. 7B illustrates an alternative example environment for generating an image of the rectangular FOV.
Figure 7A:
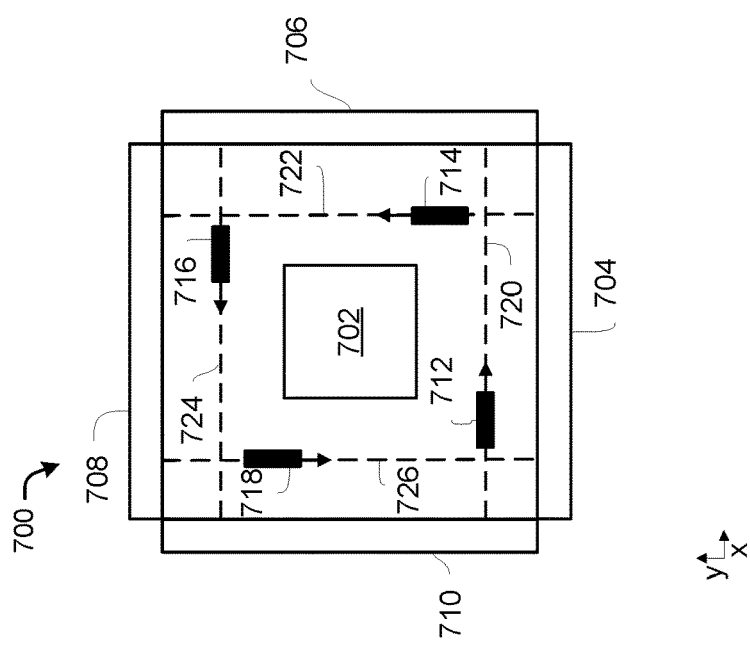
FIG. 7A illustrates an example environment for generating an image of a rectangular FOV.

FIG. 7A illustrates an example environment 700 for generating an image of a rectangular FOV 702. As shown, the environment 700 includes first through fourth arrays 704 to 710 disposed around a perimeter of the FOV 702. Each one of the arrays 704 to 710 may include multiple detectors configured to detect photon flux continuously and/or at multiple time intervals. For example, the first array 704 and the third array 708 include detectors arranged in a row extending along a first direction (e.g., an x direction) and the second array 706 and the fourth array 710 include detectors arranged along a column extending along a second direction (e.g., a y direction).

The environment 700 also includes first through fourth attenuators 712 to 718 that move along first through fourth paths 720 to 726. The first attenuator 712 moves along the first path 720 in the first direction, wherein the first path 720 is between the FOV 702 and the first array 704. The second attenuator 714 moves along the second path 722 in the second direction, wherein the second path 722 is between the FOV 702 and the second array 706. The third attenuator 716 moves along the third path 724 in the opposite of the first direction, wherein the third path 724 is between the FOV 702 and the third array 708. The fourth attenuator 718 moves along the fourth path 726 in the opposite of the second direction, wherein the fourth path 726 is between the FOV 702 and the fourth array 710.

The detectors of the first through fourth arrays 704 to 710 may detect fluxes of photons transmitted from the FOV 702 as the first through fourth attenuators 712 to 718 move along the first through fourth paths 720 to 726. Based on the fluxes detected by the detectors and the positions of the attenuators 712 to 718, an imaging system may generate a two-dimensional image of the FOV 702.

An example simulation was performed using an imaging system as illustrated in FIG. 7A. Each of the arrays 704 to 710 was 210 mm long and included 210 1.0 mm detector elements. The attenuators 712 to 718 were modeled as rectangular bars and moved in 2D planes. In a 3D implementation, the bars may move in the plane perpendicular to the x and y directions, eliminating the potential for collision between the attenuators 712 to 718 and the arrays 704 to 710 along the paths 720 to 726. The detectors within the arrays 704 to 710 and the attenuators 712 to 718 were modeled as ideal absorbers. Scatter and attenuation were not modeled.

The simulated source in the FOV 702 was modeled as a 46 mm diameter circle (background); 20 mm diameter circle (warm object) offset from the center of the large circle; and two 2 mm diameter "hot" circles, one in the background, the other in the warm object. The activity ratios of the background, warm object, and two hot spots were 1:2:20:20. $10^8$ decays were simulated as emitted isotropically from the phantom. The attenuators 712 to 718 were translated between the FOV 702 and the arrays 704 to 710 and the timestamp of each detected event was recorded. The detector pixel, and timestamp data from a simulated 5-minute acquisition were used for image reconstruction. Objects were reconstructed to 1.0 mm square image pixels. Equation 1 was iteratively solved using a likelihood-based cost function and gradient-based optimization algorithm. No post-filtering of the reconstructed image was performed and no image priors or regularization were used. The activity ratios measured from the reconstructed image between the two large circles and the two hot circles were 1.0, 2.0, 8.3, 6.8, demonstrating excellent quantitative results for the larger circles and some partial volume effects for the 2.0 mm diameter circles.

Other simulations of point sources using the system illustrated in FIG. 7A were performed. Those simulations were able to achieve <2.0 mm FWHM resolution.

FIG. 7B illustrates an alternative example environment 728 for generating an image of the rectangular FOV 702. In the example environment 728, a single array 730 and a single attenuator 732 is used to detect photons transmitted from the FOV 702. In various implementations, the single array 730 detects photon fluxes at a first position 734 as the single attenuator 732 moves along a first path 736 during a first time interval. Further, the single array 730 is moved to a second position 738. At the second position 738, the single array 730 detects photon fluxes as the single attenuator 732 moves along a second path 740 during a second time interval. Then, the single array 730 is moved to a third position 742 and detects photon fluxes as the single attenuator 732 moves along a third path 744 during a third time interval. Finally, the single array 730 is moved to a fourth position 746 and detects photon fluxes as the single attenuator 732 moves along a fourth path 748 during a fourth time interval. Based on the fluxes detected during the first through fourth time intervals, an imaging system may generate a two-dimensional image of the FOV 702.

In various implementations, the example environment 728 illustrated in FIG. 7B can be used to generate an image of the FOV 702 with equivalent resolution to the example environment 700 illustrated in FIG. 7A, but with the single array 730 rather than multiple arrays 704 to 710. However, in some cases, the acquisition time of the example environment 728 may be greater than the acquisition time of the example environment 700. Although FIGS. 7A and 7B are described with reference to generating a two-dimensional image of the FOV 702, implementations are not so limited. For example, similar techniques can be used to generate a volumetric image of a three-dimensional FOV.

Other possibilities include combinations of different shapes of attenuators, combinations of stationary and moving attenuators (e.g., collimation slats in one direction with a mechanically-controlled flux manipulation in an orthogonal direction), or any other such combination of attenuators that allows for mechanically controlled flux manipulation in order to compute local flux levels. Furthermore, the attenuators 712 to 718 and/or 732 need not be linearly translated across the FOV 702. In some cases, an attenuator 712 to 718 and/or 732 may move at variable speed, along non-linear trajectories, or be moved in any fashion to obstruct lines of response in a way that allows for computation of the sinogram. Although FIGS. 7A and 7B illustrate an example in which the positions of the arrays 704 to 710 and 734 and/or paths of the attenuators 712 to 718 and/or 732 follow a square shape, implementations are not so limited. For instance, the positions of the arrays 704 to 710 and 734 and/or paths of the attenuators 712 to 718 and/or 732 may form a triangular shape, a rectangular shape, a pentangular shape, a hexagonal shape, or a circular shape, or the like.

FIG. 8A illustrates an example environment 800 of a single detector 802 detecting a flux of photons emitted by a first source 804 and a second source 806 during an acquisition time. A single attenuator 808 is moved along a path 810 during the acquisition time. FIG. 8B illustrates a distribution 812 of the flux detected by the detector 802 during the acquisition time. The y-axis of the distribution 812 represents flux detected by the detector 802 and the x-axis of the distribution 812 represents the position of the attenuator 808 along the path 810. If the attenuator 808 moves at a constant velocity or speed, the x-axis may also represent time during the acquisition time. In various cases, the path 810 of the attenuator 808 crosses at least one first LOR extending between the detector 802 and the first source 804, as well as at least one second LOR extending between the detector 802 and the second source 804.

As shown, the distribution 812 is initially at a relatively high level, indicating that the attenuator 808 is exposing the first source 804 and the second source 806 of the photons that are transmitted toward the detector 802. The distribution 812 then dips to a lower level that includes a substantially constant flux across a range of positions of the attenuator 808. This may indicate that the attenuator 808 is fully blocking the first source 804 of photons but is still exposing the second source 806 of photons. Next, the distribution 812 dips to its lowest level. This may indicate that the attenuator 808 is blocking the first source 804 and the second source 806 of photons simultaneously. Next, the distribution 812 rises to a higher level, indicating that the attenuator 808 is exposing the first source 804 but still blocking the second source 806. Finally, the distribution 812 returns to the initial, relatively high level, indicating that the attenuator 808 is once again exposing the first source 804 and the second source 806 of photons. Based on the distribution 812, as well as the positions of the attenuator 808 throughout the acquisition time, an imaging system may generate an image of an FOV including the first source 804 and the second source 806.

Figure 9:
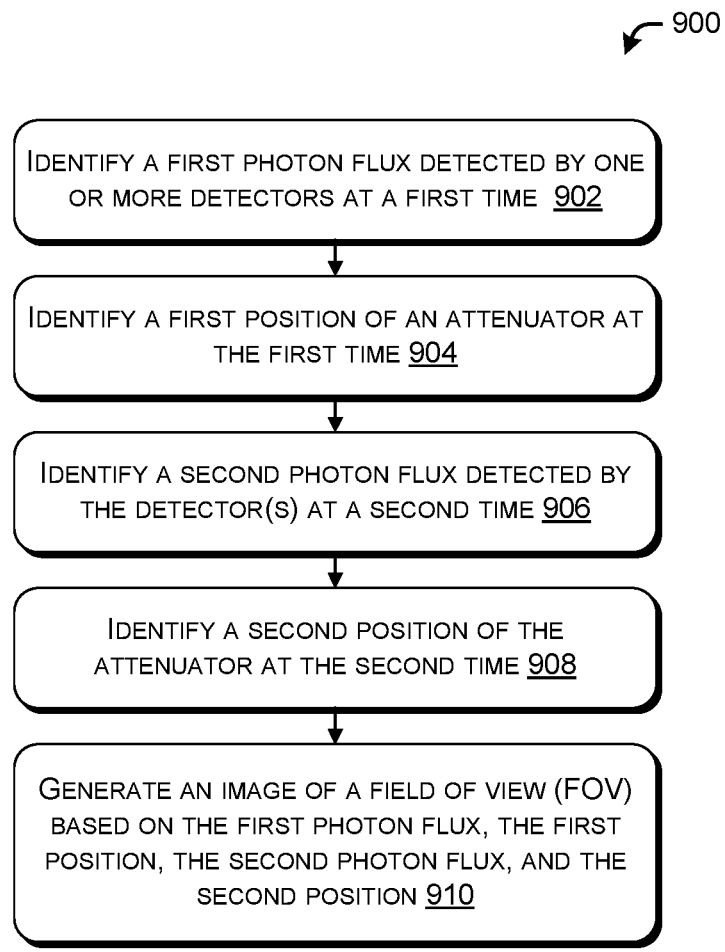
FIG. 9 illustrates an example process for generating a SPECT image based on photon flux.
Figure 10:
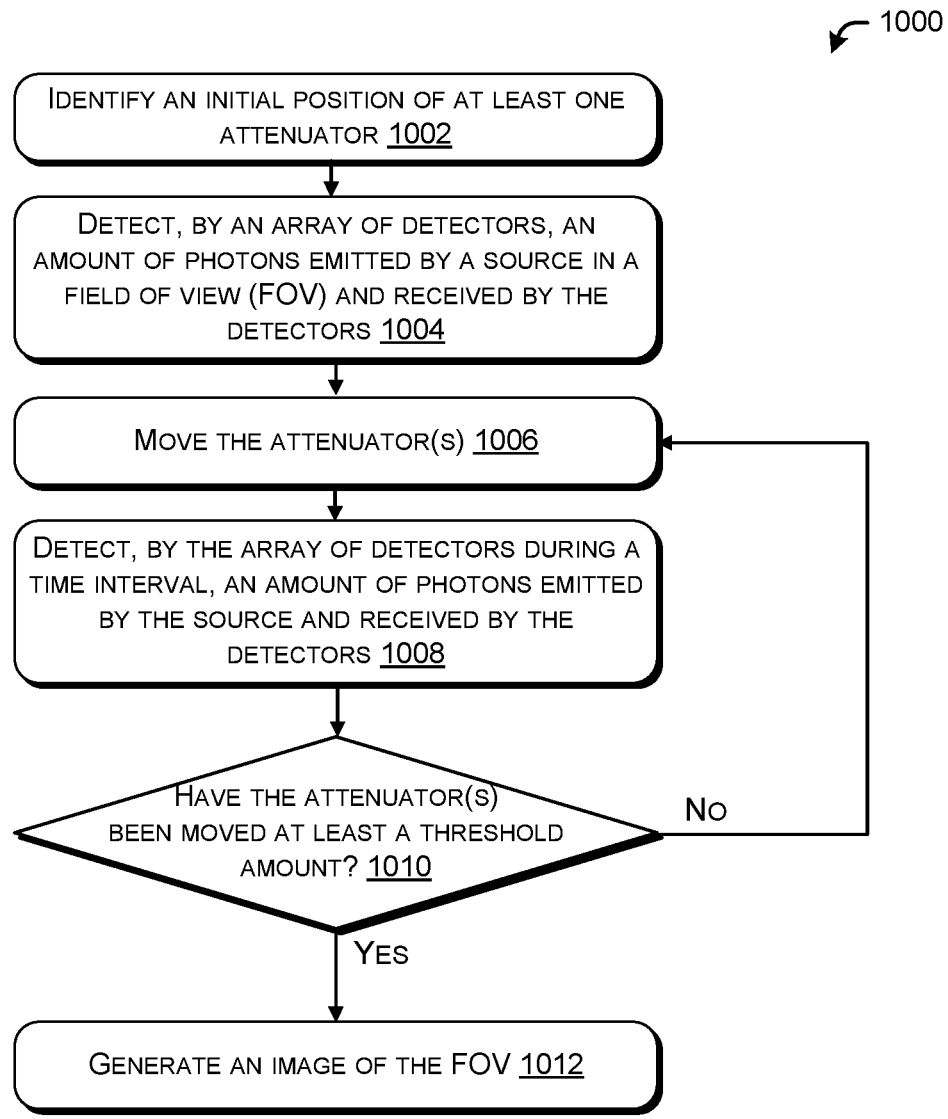
FIG. 10 illustrates an example process for generating a SPECT image using a moving attenuator.

FIGS. 9 and 10 illustrate example processes in accordance with implementations of the present disclosure. Although the processes illustrated in FIGS. 9 and 10 include steps arranged in specific orders, implementations are not limited to the specific orders shown in FIGS. 9 and 10.

FIG. 9 illustrates an example process 900 for generating a SPECT image based on photon flux. The process 900 may be performed by an entity, such as a SPECT imaging system and/or the image processing system 114 described above with reference to FIG. 1.

At 902, the entity identifies a first photon flux detected by one or more detectors at a first time. The first photon flux may represent a number of photons received by each detector during the first time. The first time, for instance, may be a time interval. In some examples, the first photon flux is detected by multiple detectors in an array. According to various implementations, the photons may be transmitted by a source, such as one or more radiotracers disposed in a body of a subject. The source may be disposed within a field of view (FOV) of the detector(s). In various implementations, the source may emit x-rays, gamma rays, or a combination thereof.

In some cases, the detector(s) includes an array of detectors. The detectors may be arranged in one or more rows and one or more columns. In some cases, the detectors are disposed in an arc. The radius of the arc may extend toward the FOV of the detector(s). In some examples, an individual detector includes an individual crystal (e.g., sodium iodide, cesium iodide, cadmium zinc telluride, cadmium telluride, lutetium-yttrium oxyorthosilicate (LYSO), cerium-doped lutetium oxyorthosilicate (LSO), lutetium fine silicate (LFS), or any combination thereof) configured to generate a visible light photon in response to receiving an x-ray or gamma ray photon from a source. The individual detector may further include a sensor configured to detect the visible light photon. In some implementations, multiple detectors include respective sodium iodide crystals, wherein a barrier is disposed between adjacent sodium iodide crystals. Accordingly, a visible light photon generated by one crystal may be blocked from traveling to an adjacent crystal. In some cases, the detector(s) include cerium-doped multicomponent gadolinium aluminum gallium garnet (Ce:GAGG), an alloy of cadmium telluride and cadmium zinc telluride, or silicon. For example, the detector(s) may include silicon photomultipliers.

The detector(s) may receive the photons from the source at various angles. For example, a photon may be received by an individual detector at an angle that is greater than 0 degrees and less than or equal to 97 degrees, wherein the angle is defined between a sensing face of the individual detector and the path of the photon. In some implementations, an individual detector may receive multiple (e.g., at least two photons) with paths that form at least one angle that is at least 5 degrees and less than 45 degrees, 90 degrees, 135 degrees, or 180 degrees. Thus, the individual detector may receive photons from a broad range of angles during the first time.

At 904, the entity identifies a first position of an attenuator at the first time. The attenuator, in some examples, may be at least partially disposed between the source and the detector(s). In some cases, the attenuator may block one or more LORs extending between the source and the detector(s). The attenuator may absorb or otherwise attenuate photons transmitted by the source along the LOR(s). For example, the attenuator may include lead, tungsten, uranium, or a combination thereof. Accordingly, the first position of the attenuator may impact the magnitude of the first photon flux detected by the multiple detectors at the first time. In some cases, the attenuator is no longer than a length of the array of detectors. In some implementations, the length of the attenuator is at least 10% of the length of the array of detectors.

In various implementations, the attenuator is not a collimator. For example, in some implementations, the attenuator lacks holes or apertures. For instance, the attenuator may be nonporous. In some implementations, the attenuator includes a prismatic shape, such as a rectangular or circular prism.

In some cases, the attenuator is one of multiple attenuators at least partially blocking the photons emitted by the source from reaching the detector(s) at the first time. In various examples, a first attenuator and a second attenuator are separated by a distance that is greater than or equal to 1 millimeter (1 mm) and less than or equal to the length of the array.

At 906, the entity identifies a second photon flux detected by the detector(s) at a second time. The second photon flux may represent a number of photons received by each detector during the second time. The second time, for instance, may be a time interval. In some examples, the second photon flux is detected by multiple detectors in the array. According to various implementations, the photons may be transmitted by the source.

At 908, the entity identifies a second position of the attenuator at the second time. In various implementations, the second position is different than the first position. For example, an actuator may move the attenuator from the first position to the second position between the first time and the second time. Due to the changed position of the attenuator, the second flux may be different than the first flux. For instance, at the second time, the attenuator may block one or more LORs extending between the source and the detector(s), wherein the attenuator blocks different LORs during the first time than during the second time.

In various implementations, the detector(s) include an individual detector with a line-of-sight that is fully exposed to the source by the attenuator during the first time and is fully blocked from the source by the attenuator during the second time. For example, if the first and second photon fluxes are detected by the individual detector, the first photon flux is nonzero and/or above a threshold and the second photon flux is zero and/or below the threshold. The threshold, for instance, may correspond to a minimal amount of photon flux from scattered photons that would be detected by the individual detector when the detector is fully blocked from the source. In some cases, the detector(s) include an individual detector with a line-of-sight that is fully blocked from the source by the attenuator during the first time and is fully exposed to the source by the attenuator during the second time. For example, if the first and second photon fluxes are detected by the individual detector, the first photon flux is nonzero and/or above a threshold and the second photon flux is zero and/or below the threshold.

At 910, the entity generates an image of an FOV based on the first photon flux, the first position, the second photon flux, and the second position. The image may be a two-dimensional image including multiple pixels depicting the distribution of the source of the photons within respective regions of the FOV. In some cases, the image is a three-dimensional, volumetric image including multiple voxels depicting the distribution of the source of the photons within respective regions of the FOV.

In some cases, the entity generates the image based on a probability distribution. In various implementations, the entity may generate the probability distribution based on the probability that different regions within the FOV contain the source of the photons. The entity may calculate a probability of a particular region based on the first photon flux and the second photon flux. For example, if the first photon flux and the second photon flux detected by a first detector are substantially unchanged, then the probability assigned to a region within the FOV corresponding to an LOR that has been blocked or exposed between the first and second times may be relatively low. In contrast, if the first photon flux detected by a second detector is substantially greater than the second photon flux detected by the second detector, then the probability of a region corresponding to an LOR that was exposed during the first time and blocked during the second time may be relatively high. In various implementations, the entity assigns the values of the pixels or voxels of the image based on the probabilities corresponding to the pixels or voxels.

In some implementations, the entity generates the image based on a derivative of the first and second fluxes with respect to time. For instance, the entity may generate a discrete derivative of the photon fluxes detected by the detector(s) by determining a first difference between the first flux and the second flux, a second difference between the first time and the second time, and a quotient including the first difference divided by the second difference. If the first flux represents fluxes detected by multiple detectors at the first time, and the second flux represents fluxes detected by the multiple detectors at the second time, then the quotient may include multiple quotients. According to some cases, the entity may generate one or more continuous derivatives of the fluxes detected by the detector(s) over time. In some cases, the entity generates a distribution of flux-per-LOR for each detector, wherein each detector is associated with multiple LORs respectively extending from regions of the FOV. The distribution of flux-per-LOR can be generated based on the quotients and/or time derivatives (e.g., radon inversion, though X-ray, fan beam, or another inversion can be used). The entity may arrange the LOR-flux data into a tomographic dataset (e.g., a sinogram or similar structure) and reconstruct the image of the FOV using one or more image reconstruction algorithms (FBP, MLEM, etc.) on the tomographic dataset. According to various implementations, the entity generates a sinogram based on the discrete quotients and/or time derivatives of the fluxes detected by the detector(s).

In some cases, the maximum quotients can correspond to detectors whose LORs were exposed between the first time and the second time. Similarly, the minimum quotients can correspond to detectors whose LORs were blocked between the first time and the second time. In various implementations, the entity can assign values to the pixels or voxels of the image based on regions of the FOV corresponding to the exposed and blocked LORs.

In some examples, the entity generates the image based on a matrix-based equation. For instance, the entity may generate a systems matrix (P) based on the position of the detector(s) and the first and second positions of the attenuator. P may include the sensitivity of each of the detector(s) to regions of the FOV at the first time (when the attenuator is in the first position), as well as the sensitivity of each of the detector(s) to the regions of the FOV at the second time (when the attenuator is in the second position). The entity may further generate a data array (g) that includes the first flux and the second flux. The entity may generate an image array (f) by solving Pf=g, wherein the elements of f correspond to the values of the pixels or voxels in the image.

In various implementations, the entity may output the image of the FOV and/or transmit data indicative of the image to a computing device. In some cases, the entity includes a display (e.g., a screen) configured to visually output the image of the FOV. According to some examples, the entity may include a transmitter configured to transmit the data to the computing device.

FIG. 10 illustrates an example process 1000 for generating a SPECT image using a moving attenuator. The process 1000 may be performed by an entity, such as a SPECT imaging system, or the arrays 110, the detectors 112, the image processing system 114, the attenuators 116, and the movement system 118 described above with reference to FIG. 1.

At 1002, the entity identifies an initial position of at least one attenuator. The attenuator(s), in some examples, may be at least partially disposed between an array of detectors and an FOV of the array. A source of photons may be disposed in the FOV. In some cases, the attenuator(s) may block one or more LORs extending between the source and the detectors. The attenuator(s) may absorb or otherwise attenuate photons transmitted by the source along the LOR(s). For example, the attenuator(s) may include lead, tungsten, uranium, or a combination thereof. In some cases, an individual attenuator is no longer than the length of the array of detectors. In some implementations, the length of the individual attenuator is at least 10% of the length of the array of detectors.

In various implementations, the attenuator(s) do not include a collimator. For example, in some implementations, the attenuator(s) lack holes or apertures. For instance, the attenuator(s) may include one or more nonporous objects. In some implementations, an example attenuator includes a prismatic shape, such as a rectangular or circular prism. In various examples, a first attenuator and a second attenuator are separated by a distance that is greater than or equal to 1 mm and less than or equal to the length of the array.

At 1004, the entity detects, by the array of detectors, an amount of photons emitted by the source and received by the detectors at the initial time. In various implementations, the entity detects, by a single detector, the amount of photons received by the single detector at the initial time. For example, the entity detects the flux of photons received by the single detector at the initial time. In some cases, the entity detects the flux of photons received by each detector in the array at the initial time.

At 1006, the entity moves the attenuator(s). For example, the attenuator(s) may be moved by an actuator. In various implementations, the entity may move the attenuator(s) with respect to the FOV of the array. For instance, the entity may move the attenuator(s) in a first direction that crosses a second direction extending from the array to the FOV. In some implementations, the entity moves the attenuator(s) with respect to the array. For example, the entity may move the attenuator(s) in a direction parallel to at least one sensing face of the detectors in the array.

At 1008, the entity detects, by the array of detectors during a time interval, an amount of photons emitted by the source and received by the detectors. In various implementations, the entity detects, by a single detector, the amount of photons received by the single detector during the time interval. For example, the entity detects the flux of photons received by the single detector during the time interval. In some cases, the entity detects the flux of photons received by each detector in the array during the time interval.

At 1010, the entity determines whether the attenuator(s) have been moved at least a threshold amount. In various implementations, the threshold amount may correspond to an amount associated with the attenuator(s) exposing and blocking at least one of the detectors to each region of the FOV. For example, the FOV may include multiple regions corresponding, respectively, to pixels or voxels of an image to be generated of the FOV. During image acquisition, at least one detector detects at least one flux of photons when each region is exposed by the attenuator(s) and detects at least one flux of photons with the corresponding region is blocked by the attenuator(s). For example, the threshold amount may correspond to a position at which the attenuator(s) blocks LORs from a region to an individual detector, as well as a position at which the attenuator(s) expose the LORs from the region to the individual detector. Accordingly, the entity may be able to discern the presence of the source in each one of the regions of the FOV, based on the fluxes detected by the array of detectors. In various implementations, the threshold amount depends on the size of the FOV, the number of regions in the FOV, the number of detectors, the distance between attenuators, the size of the attenuator(s), the distance between the attenuator(s) and the FOV, the distance between the attenuator(s) and the array, and so on.

If the entity determines that the attenuator(s) have not been moved at least the threshold amount at 1010, the process returns to 1006. That is, image acquisition is continued by moving the attenuator(s) at 1006 and detecting the resultant fluxes of photons received by the detectors at 1008.

If, on the other hand, the entity determines that the attenuator(s) have been moved at least the threshold amount at 1010, then the process proceeds to 1012. At 1012, the entity generates an image of the FOV. The image may be a two-dimensional image including multiple pixels depicting the distribution of the source of the photons within respective regions of the FOV. In some cases, the image is a three-dimensional, volumetric image including multiple voxels depicting the distribution of the source of the photons within respective regions of the FOV.

In some cases, the entity generates the image based on a probability distribution. In various implementations, the entity may generate the probability distribution based on the probability that different regions within the FOV contain the source of the photons. The entity may calculate a probability of a particular region based on the fluxes detected by the detectors that were exposed and blocked by the attenuator(s) during image acquisition. For example, if a first photon flux and a second photon flux detected by a first detector are substantially unchanged, then the probability assigned to a region within the FOV corresponding to an LOR that has been blocked or exposed between acquisition of the first and second photon fluxes may be relatively low. In contrast, if a third photon flux detected by a second detector is substantially greater than the fourth photon flux detected by the second detector, then the probability of a region corresponding to an LOR that was exposed when the third photon flux was acquired and blocked when the fourth photon flux was acquired may be relatively high. In various implementations, the entity assigns the values of the pixels or voxels of the image based on the probabilities corresponding to the pixels or voxels.

In some implementations, the entity generates the image based on derivatives of the fluxes with respect to time. For instance, the entity may calculate the derivatives of the fluxes detected by each detector over time. The entity may generate a distribution of flux-per-LOR for each detector, wherein each detector is associated with multiple LORs respectively extending from regions of the FOV, and the distribution of flux-per-LOR can be generated by taking the derivative of the flux detected by each detector with respect to time in order to obtain differential flux rates for each detector (e.g., Radon inversion, although X-ray, fan beam or another inversion can be used). In some cases, the entity may arrange the LOR-flux data into a tomographic dataset (e.g., a sinogram or similar structure) and reconstruct the image of the FOV using one or more image reconstruction algorithms (FBP, MLEM, etc.) on the tomographic dataset.

In some cases, the maximums of the flux derivatives can correspond to times and positions of the attenuator(s) that expose LORs of the corresponding detectors. Similarly, the minimums of the flux derivatives can correspond to times and positions of the attenuator(s) that block LORs of the corresponding detectors. In various implementations, the entity can assign values to the pixels or voxels of the image based on regions of the FOV corresponding to the exposed and blocked LORs.

In some examples, the entity generates the image based on a matrix-based equation. For instance, the entity may generate a systems matrix (P) based on the positions of the detectors and the positions of the attenuator during image acquisition. P may include the sensitivity of each of the detectors to regions of the FOV at the different time intervals at which fluxes were detected, wherein the sensitivities correspond to the positional relationships between the detectors, the regions, and the attenuator(s) at the different time intervals. The entity may further generate a data array (g) that includes the fluxes. The entity may generate an image array (f) by solving Equation 1 wherein the elements of f correspond to the values of the pixels or voxels in the image.

In various implementations, the entity may output the image of the FOV and/or transmit data indicative of the image to a computing device. In some cases, the entity includes a display (e.g., a screen) configured to visually output the image of the FOV. According to some examples, the entity may include a transmitter configured to transmit the data to the computing device.

Figure 11:
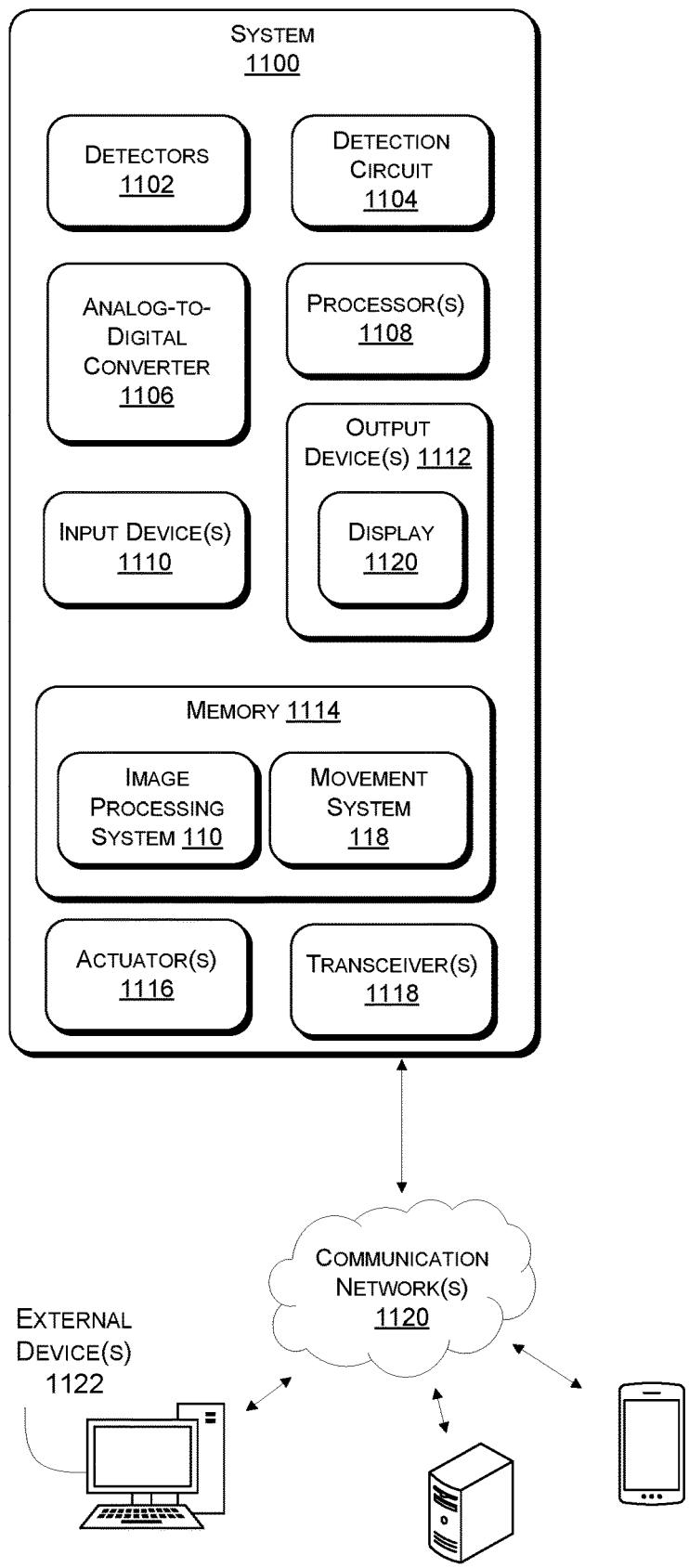
FIG. 11 illustrates an example system configured to perform various methods and functions disclosed herein.

FIG. 11 illustrates an example system 1100 configured to perform various methods and functions disclosed herein. The system 1100 includes detectors 1102, a detection circuit 1104, an analog-to-digital converter 1106, one or more processors 1108, one or more input devices 1110, one or more output devices 1112, memory 1114, one or more actuators 1116, and one or more transceivers 1118. In some implementations, any of these components may be omitted from the system 1100.

The detectors 1102 may be configured to receive photons from an FOV of the system 1100. The photons, for example, may be x-rays, gamma rays, or a combination thereof. In various implementations, the detectors 1102 may be configured to generate analog signals based on the photons they receive from the FOV.

The detection circuit 1104 may be an electrical circuit configured to receive the analog signals generated by the detectors 1102. In various examples, the detection circuit 1104 may include one or more analog filters configured to filter the analog signals. In some cases, the detection circuit 1104 includes a thresholding circuit configured to filter out analog signals generated based on photons received by the detectors 1102 at energy levels below a threshold energy level. Accordingly, the system 1100 may ignore photons from the FOV that have been scattered before reaching the detectors 1102.

The analog-to-digital converter 1106 may convert the analog signals from the detection circuit 1104 into one or more digital signals. The analog-to-digital converter may provide the digital signal(s) to the processor(s) 1108 for further processing. The digital signal(s) may be indicative of the fluxes of photons detected by the detectors 1102 over time.

In some implementations, the processor(s) 1108 include a central processing unit (CPU), a graphics processing unit (GPU), or both CPU and GPU, or other processing unit or component known in the art. The processor(s) 1108 may be configured to execute instructions stored in the memory 1114, in various implementations. In some examples, the processor(s) 1108 are configured to generate an image of the FOV based on the digital signal(s) generated by the analog-to-digital converter 1106.

The input device(s) 1110 may include, for instance, a keypad, a cursor control, a touch-sensitive display, voice input device, etc. In some implementations, the input device(s) 1110 are configured to receive an input signal (e.g., from a user) requesting a relatively high-resolution image of a portion of the FOV. The input device(s) 1110 may be communicatively coupled to the processor(s) 1108 and may indicate the input signal to the processor(s) 1108. The output device(s) 1112 may include, for example, a display 1120, speakers, printers, etc. The output device(s) 1112 may be communicatively coupled to the processor(s) 1108. In various implementations, the display may be configured to output the image of the FOV generated by the processor(s) 1108.

The memory 1114 may include various instruction(s), program(s), database(s), software, operating system(s), etc. In some implementations, the memory 1114 includes instructions that are executed by processor(s) 1108 and/or other components of the system 1100. For example, the memory 1114 may include software for executing functions of the image processing system 110 and/or movement system 118 described above with reference to FIG. 1. For example, the processor(s) 1108, upon executing instructions of the image processing system 110, may be configured to generate an image of the FOV based on the digital signal(s) generated by the analog-to-digital converter 1106. In some cases, the processor(s) 1108 may further generate the image based on one or more signals from the actuator(s) 1116, which may be indicative of positions of one or more attenuators at least partially disposed between the FOV and the detectors 1102. According to some examples, the instructions in the movement system 118, when executed by the processor(s) 1108, may cause the processor(s) 1108 to perform operations including controlling the actuator(s) 1116 to move the attenuator(s) (e.g., at a particular speed, in a particular position, etc.).

The device system 1100 include additional data storage devices (removable and/or non-removable) such as, for example, magnetic disks, optical disks, or tape. Tangible computer-readable media can include volatile and non-volatile, removable and non-removable media implemented in any method or technology for storage of information, such as computer readable instructions, data structures, program modules, or other data. The memory 1114, the removable storage, and the non-removable storage are all examples of computer-readable storage media. Computer-readable storage media include, but are not limited to, Random Access Memory (RAM), Read-Only Memory (ROM), Electrically Erasable Programmable Read-Only Memory (EEPROM), flash memory, or other memory technology, Compact Disk Read-Only Memory (CD-ROM), Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the system 1100. Any such tangible computer-readable media can be part of the system 1100. In some examples, the processor(s) 1108 may be configured to perform various functions described herein based on instructions stored on a non-transitory computer readable medium.

In various implementations, the actuator(s) 1116 may include one or more motors configured to move the attenuator(s). The actuator(s) 1116 may be communicatively coupled with the processor(s) 1108.

The system 1100 be configured to communicate over a telecommunications network using any common wireless and/or wired network access technology. For example, the transceiver(s) 1118 can include a network interface card (NIC), a network adapter, a Local Area Network (LAN) adapter, or a physical, virtual, or logical address to connect to various network components, for example. To increase throughput when exchanging wireless data, the transceiver(s) 1118 can utilize multiple-input/multiple-output (MIMO) technology. The transceiver(s) 1118 can comprise any sort of wireless transceivers capable of engaging in wireless, radio frequency (RF) communication. The transceiver(s) 1118 can also include other wireless modems, such as a modem for engaging in Wi-Fi, WiMAX, Bluetooth, infrared communication, and the like. The transceiver(s) 1118 may include transmitter(s), receiver(s), or both. In various implementations, the transceiver(s) 1118 can transmit data over one or more communication networks 1120, such as at least one Wi-Fi network, at least one WiMAX network, at least one Bluetooth network, at least one cellular network, one or more wide area networks (WANs), such as the Internet, or the like. The transceiver(s) 1118 may transmit the data to one or more external devices 1122, such as external computing devices. The transceiver(s) 1118 may be communicatively coupled to the processor(s) 1108. For example, the processor(s) 1108 may generate data indicative of the image of the FOV, and the transceiver(s) 1118 may transmit that data to the external device(s) 1122.

The system 1100 may be configured to communicate over the communications network(s) 1120 using any common wireless and/or wired network access technology. Moreover, the system 1100 may be configured to run any compatible device Operating System (OS), including but not limited to, Microsoft Windows Mobile, Google Android, Apple iOS, Linux Mobile, as well as any other common mobile device OS.

Although various implementations are described herein with reference to SPECT and PET tomography, it will be obvious to persons of skill in the art, based on the present disclosure, that the disclosed systems may be used to perform tomosynthesis (e.g., high resolution limited-angle tomography), other planar imaging, or non-tomographic imaging as is known in the art. Any method that utilizes an attenuating object that is systematically moved during image acquisition so as to alter detector flux and thus enables the creation of an imaging dataset or enables the computation of flux or count rates from specific lines of response is contemplated.

Various noncollimated imaging systems described herein can be used for PET imaging. In PET, two anti-parallel photons are detected in a pair and the line of response used in image reconstruction is determined by the positions of the two photon interactions. If an attenuator is removed from a detector, the fully exposed detectors can act as PET detectors. Alternatively, the PET data can be acquired with the attenuator in use and the PET data adjusted for the loss of flux accordingly. The photons used in PET can be 511 keV each, and are generally much higher energy than the photons used in SPECT imaging. If both a PET and SPECT tracer are in the field of view at the same time, discriminating between the PET and SPECT photon energies could allow for the simultaneous acquisition of both SPECT and PET data.

Example Clauses

1. A single photon emission computed tomography (SPECT) system including: a bed configured to support a subject, a source being disposed inside of the subject; an array of detectors configured to detect first photons emitted from the source over time; an attenuator disposed between the array of detectors and the source, the attenuator being nonporous, spaced apart from the array of detectors, and configured to attenuate second photons emitted from the source; an actuator configured to change a position of the attenuator relative to the source over time; at least one processor; and memory storing instructions that, when executed by the at least one processor, cause the at least one processor to perform operations including: generating an image of the source based on the first portion of the photons detected by the array of detectors over time and the position of the attenuator over time.
2. The SPECT system of clause 1, wherein the bed includes a material that is transparent to at least a portion of the first photons and at least a portion of the second photons.
3. The SPECT system of clause 1 or 2, wherein the array of detectors includes rows of detectors extending in a first direction and columns of detectors extending in a second direction, and wherein the actuator is configured to change the position of the attenuator along the first direction and/or the second direction.
4. The SPECT system of any one of clauses 1 to 3, wherein the array of detectors includes an arc of detectors, a radius of the arc extending toward the bed.
5. The SPECT system of any one of clauses 1 to 4, wherein the array of detectors includes scintillator crystals coupled to respective sensors, the scintillator crystals being configured to generate third photons based on the first photons.
6. The SPECT system of clause 5, wherein a barrier is disposed between a first crystal among the scintillator crystals and a second crystal among the sodium iodide crystals, the barrier including a material configured to reflect at least a portion of the third photons.
7. The SPECT system of any one of clauses 1 to 6, wherein the array of detectors includes crystals including at least one of cerium-doped multicomponent gadolinium aluminum gallium garnet (Ce:GAGG) or an alloy of cadmium telluride and zinc telluride.
8. The SPECT system of any one of clauses 1 to 7, wherein the first photons and the second photons include gamma rays.
9. The SPECT system of any one of clauses 1 to 8, wherein a particular detector among the detectors is configured to detect a first amount of the first photons received by the particular detector during a first time interval and to detect a second amount of the first photons received by the particular detector during a second time interval, wherein the actuator is configured to move the attenuator from a first position during the first time interval to a second position during the second time interval, and wherein the processor is configured to generate the image based on the first amount of the first photons, the first position of the actuator, the second amount of the first photons, and the second position of the actuator.
10. The SPECT system of clause 9, wherein the first amount of the first photons is greater than a threshold, and wherein the second amount of the first photons is less than the threshold.
11. The SPECT system of clause 9 or 10, wherein the image includes a pixel or voxel corresponding to a region of a field of view (FOV), and wherein the processor is configured to generate the image by: determining a first sensitivity of the particular detector to one or more lines of response (LORs) extending from the region of the FOV to the particular detector at the first time interval based on the first position of the attenuator relative to the one or more LORs; determining a second sensitivity of the particular detector to the one or more LORs extending from the region of the FOV to the particular detector at the second time interval based on the second position of the attenuator relative to the one or more LORs, the first sensitivity being different than the second sensitivity; and determining a value of the pixel or voxel based on the first sensitivity, the second sensitivity, the first amount, and the second amount.
12. The SPECT system of any one of clauses 1 to 11, wherein a particular detector among the detectors is configured to detect at least one of the first photons received by a sensing face of the particular detector at an angle that is greater than about 0 degrees and that is less than or equal to about 87 degrees.

13. The SPECT system of any one of clauses 1 to 12, wherein the attenuator includes at least one of lead, uranium, or tungsten.
14. The SPECT system of any one of clauses 1 to 13, wherein a length of the attenuator is greater than about 10% of a length of the array of detectors and is less than about the length of the array of detectors.
15. The SPECT system of any one of clauses 1 to 14, further including: multiple attenuators disposed between the array of detectors and the source.
16. The SPECT system of clause 15, wherein a spacing between a first attenuator among the multiple attenuators and a second attenuator among the multiple attenuators is greater than about 1 millimeter (mm) and less than about a length of the array of detectors.
17. The SPECT system of any one of clauses 1 to 16, wherein the attenuator includes a polygonal prism or a circular prism.
18. The SPECT system of any one of clauses 1 to 17, wherein the actuator is a first actuator configured to move the attenuator in a first direction, and wherein the SPECT system further includes a second actuator configured to move in a second direction, the second direction crossing the first direction: the attenuating object and the array of detectors; or the bed.
19. The SPECT system of any one of clauses 1 to 18, wherein the actuator is a first actuator, and wherein the SPECT system further includes a second actuator configured to move the array of detectors in a direction that is different than the direction in which the first actuator moves the attenuator.
20. The SPECT system of any one of clauses 1 to 19, wherein the actuator is configured to change the position of the attenuator at a first speed and at a second speed, the first speed being slower than the second speed.
21. The SPECT system of clause 20, further including: an input device configured to receive an input signal indicating a region within the field-of-view (FOV) of the SPECT system, wherein the actuator is configured to change the position of the attenuator at the first speed when the attenuator is at least partially disposed between the array of detectors and the region of the FOV.
22. The SPECT system of any one of clauses 1 to 21, wherein the image is a three-dimensional image of a field-of-view (FOV) of the SPECT system, the FOV including the source.
23. The SPECT system of any one of clauses 1 to 22, wherein the image is indicative of a physiological structure and/or a physiological function of the subject.
24. The SPECT system of any one of clauses 1 to 23, wherein generating the image includes: determining a first number of the first photons received by a particular detector among the detectors during a first time interval that includes a first time; determining a second number of the first photons received by the particular detector during a second time interval that includes a second time; determining a first difference between the first number and the second number; determining a second difference between the first time and the second time; determining a quotient including the first difference divided by the second difference; generating a flux-per-line of response (LOR) distribution based on the quotient; and generating the image by applying filtered backprojection (FBP) or maximum likelihood estimation method (MLEM) to the flux-per-LOR distribution.
25. The SPECT system of any one of clauses 1 to 24, wherein generating the image includes: determining a derivative of a flux of the first photons detected by a particular detector among the detectors with respect to time; and generating the image based on the derivative of the flux.
26. The SPECT system of any one of clauses 1 to 25, wherein generating the image includes: generating, based on the position of the attenuator, a systems matrix (P) including sensitivities of the detectors to lines of response (LORs) extending from regions of a field-of-view (FOV), the regions of the FOV respectively corresponding to pixels or voxels of the image; generating a data array (g) including fluxes of the first photons detected by the detectors during the multiple time intervals; and determine an image array (f) based on the following equation: Pf=g, and wherein f includes values of the pixels or voxels of the image.
27. The SPECT system of any one of clauses 1 to 26, further including: a display configured to output the image; and a transceiver configured to transmit data indicative of the image to an external device.
28. The SPECT system of any one of clauses 1 to 27, wherein the SPECT system is a noncollimated SPECT system and the attenuator is not a collimator.
29. A medical imaging device, including: an array of detectors configured to detect a flux of first photons emitted from a source over time; and an attenuator disposed between the array of detectors and the source, the attenuator being configured to move over time and to attenuate second photons emitted from the source.
30. The medical imaging device of clause 29, wherein the array of detectors includes at least one row of the detectors extending in a first direction and at least one column of the detectors extending in a second direction.
31. The medical imaging device of clause 30, wherein the attenuator is configured to move in at least one of the first direction or the second direction.
32. The medical imaging device of any one of clauses 29 to 31, wherein the array of detectors includes an arc of detectors.
33. The medical imaging device of any one of clauses 29 to 32, wherein the array of detectors includes crystals coupled to respective sensors.
34. The medical imaging device of clause 33, wherein a barrier is disposed between a first crystal among the crystals and a second crystal among crystals, the barrier including a material configured to reflect at least a portion of the first photons.
35. The medical imaging device of any one of clauses 29 to 34, wherein the array of detectors includes at least one of cerium-doped multicomponent gadolinium aluminum gallium garnet (Ce:GAGG) or an alloy of cadmium telluride and zinc telluride.
36. The medical imaging device of any one of clauses 29 to 35, wherein the first photons and the second photons include at least one of gamma rays or x-rays.
37. The medical imaging device of any one of clauses 29 to 36, wherein a particular detector among the detectors is configured to detect a first amount of the first photons received by the particular detector during a first time interval and to detect a second amount of the first photons received by the particular detector during a second time interval, and wherein the attenuator is located at a first position during the first time interval and is located at a second position during the second time interval.
38. The medical imaging device of clause 37, wherein the first amount of the first photons is greater than a threshold, and wherein the second amount of the first photons is less than the threshold.
39. The medical imaging device of any one of clauses 29 to 38, wherein a particular detector among the detectors is configured to detect at least one of the first photons at an angle that is greater than about 0 degrees and that is less than or equal to about 87 degrees, the angle being defined between a sensing face of the particular detector and the at least one of the first photons as-received by the sensing face.
40. The medical imaging device of any one of clauses 29 to 39, wherein the attenuator includes at least one of lead, uranium, or tungsten.
41. The medical imaging device of any one of clauses 29 to 40, wherein a length of the attenuator is greater than about 10% of a length of the array of detectors and is less than about the length of the array of detectors.
42. The medical imaging device of any one of clauses 29 to 41, wherein the attenuator is a first attenuator, the medical imaging device further including: a second attenuator configured to move over time and to attenuate third photons emitted from the source.
43. The medical imaging device of clause 42, wherein a spacing between the first attenuator and the second attenuator is greater than about 1 millimeter (mm) and less than about 15 centimeters (cm).
44. The medical imaging device of any one of clauses 29 to 43, wherein the attenuator includes a polygonal prism or a circular prism.
45. The medical imaging device of any one of clauses 29 to 44, wherein the attenuator is nonporous.
46. A method including: identifying first data indicative a flux of photons detected by an array of detectors over time, the photons being emitted from a source and at least partially transmitted through a field-of-view (FOV); identifying second data indicative of a position of an attenuator over time, the position of the attenuator changing over time and being disposed between the FOV and the array of detectors; and generating an image of the FOV based on the first data and the second data.
47. The method of clause 46, wherein the first data is indicative of: a first amount of the photons received by a particular detector among the array of detectors during a first time interval; and a second amount of the photons received by the particular detector during a second time interval, wherein the second data is indicative of: a first position of the attenuator during the first time interval; and a second position of the attenuator during the second time interval, the second position being different than the first position, and wherein generating the image of the FOV is based on the first amount, the first position, the second amount, and the second position.
48. The method of clause 47, wherein the first amount of the photons is greater than a threshold, and wherein the second amount of the photons is less than the threshold.
49. The method of any one of clauses 46 to 48, wherein the image includes a volumetric image of the FOV, the FOV including the source.
50. The method of any one of clauses 46 to 49, wherein generating the image of the FOV includes: determining, based on the first data, a first number of the photons received by a particular detector among the detectors during a first time interval that includes a first time; determining, based on the first data, a second number of the photons received by the particular detector during a second time interval that includes a second time; determining a first difference between the first number and the second number; determining a second difference between the first time and the second time; determining a quotient including the first difference divided by the second difference; and generating the image based on the quotient.
51. The method of any one of clauses 46 to 50, wherein generating the image of the FOV includes: generating, based on the first data, a derivative of the flux of the photons with respect to time; and generating the image based on the derivative of the flux.
52. The method of any one of clauses 46 to 51, wherein generating the image includes: generating, based on the position of the attenuator over time, a systems matrix (P) including sensitivities of the detectors to regions of the FOV, the regions of the FOV corresponding to pixels or voxels of the image; generating a data array (g) including the amount of the photons detected by the detectors during each of multiple time intervals; and determine an image array (f) based on the following equation: P f=g, and wherein f includes values of the pixels or voxels of the image.
53. The method of clause 52, wherein a particular sensitivity among the sensitivities includes a sensitivity of a particular detector among the detectors to one or more lines-of-response (LORs) extending from a particular region among the regions of the FOV at a particular time interval among the multiple time intervals.
54. The method of clause 53, wherein generating P includes: determining the particular sensitivity based on an amount of the attenuator disposed between the particular region and the particular detector at the particular time interval.
55. The method of any one of clauses 46 to 54, wherein the method is at least one of a single photon emission computed tomography (SPECT) imaging method, an x-ray imaging method, or a positron emission tomography (PET) imaging method.
56. A computing device including: at least one processor; and memory storing instructions that, when executed by the at least one processor, cause the at least one processor to perform operations including the method of any one of clauses 46 to 54.
57. A non-transitory computer readable medium configured to store instructions for performing the method of any one of clauses 46 to 54.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. A medical imaging device, comprising:
an array of detectors configured to detect a flux of first photons emitted from a source over time; and
an attenuator disposed between the array of detectors and the source, the attenuator being configured to move over time and to attenuate second photons emitted from the source.

2. The medical imaging device of claim 1, wherein the array of detectors comprises at least one row of the detectors extending in a first direction and at least one column of the detectors extending in a second direction, and
wherein the attenuator is configured to move in at least one of the first direction or the second direction.

3. The medical imaging device of claim 1, wherein the array of detectors comprises crystals coupled to respective sensors, and
wherein a barrier is disposed between a first crystal among the crystal and a second crystal among the crystals, the barrier comprising a material configured to reflect at least a portion of the first photons.

4. The medical imaging device of claim 1, wherein the array of detectors comprises at least one of cerium-doped multicomponent gadolinium aluminum gallium garnet (Ce: GAGG) or an alloy of cadmium telluride and zinc telluride, and
wherein the first photons and the second photons comprise at least one of gamma rays or x-rays.

5. The medical imaging device of claim 1, wherein a particular detector among the detectors is configured to detect a first amount of the first photons received by the particular detector during a first time interval and to detect a second amount of the first photons received by the particular detector during a second time interval, and
wherein the attenuator is located at a first position during the first time interval and is located at a second position during the second time interval.

6. The medical imaging device of claim 1, wherein a particular detector among the detectors is configured to detect at least one of the first photons at an angle that is greater than about 0 degrees and that is less than or equal to about 87 degrees, the angle being defined between a sensing face of the particular detector and the at least one of the first photons as-received by the sensing face.

7. The medical imaging device of claim 1, wherein the attenuator comprises at least one of lead, uranium, or tungsten.

8. The medical imaging device of claim 1, wherein a length of the attenuator is greater than about 10% of a length of the array of detectors and is less than about the length of the array of detectors.

9. The medical imaging device of claim 1, wherein the attenuator is nonporous.

10. A method comprising:
identifying first data indicative a flux of photons detected by an array of detectors over time, the photons being emitted from a source and at least partially transmitted through a field-of-view (FOV);
identifying second data indicative of a position of an attenuator over time, the position of the attenuator changing over time and being disposed between the FOV and the array of detectors; and
generating an image of the FOV based on the first data and the second data.

11. The method of claim 10, wherein the first data is indicative of:
a first amount of the photons received by a particular detector among the array of detectors during a first time interval; and
a second amount of the photons received by the particular detector during a second time interval,
wherein the second data is indicative of:
a first position of the attenuator during the first time interval; and
a second position of the attenuator during the second time interval, the second position being different than the first position, and
wherein generating the image of the FOV is based on the first amount, the first position, the second amount, and the second position.

12. The method of claim 10, wherein generating the image of the FOV comprises:
determining, based on the first data, a first number of the photons received by a particular detector among the detectors during a first time interval that comprises a first time;
determining, based on the first data, a second number of the photons received by the particular detector during a second time interval that comprises a second time;
determining a first difference between the first number and the second number;
determining a second difference between the first time and the second time;
determining a quotient comprising the first difference divided by the second difference; and
generating the image based on the quotient.

13. The method of claim 10, wherein generating the image of the FOV comprises:
generating, based on the first data, a derivative of the flux of the photons with respect to time; and
generating the image based on the derivative of the flux.

14. The method of claim 10, wherein generating the image comprises:
generating, based on the position of the attenuator over time, a systems matrix (P) comprising sensitivities of the detectors to regions of the FOV, the regions of the FOV corresponding to pixels or voxels of the image;
generating a data array (g) comprising the amount of the photons detected by the detectors during each of multiple time intervals; and
determine an image array (f) based on the following equation:

$$Pf=g, \text{ and}$$

wherein f comprises values of the pixels or voxels of the image.

15. The method of claim 14, wherein a particular sensitivity among the sensitivities comprises a sensitivity of a particular detector among the detectors to one or more lines-of-response (LORs) extending from a particular region among the regions of the FOV at a particular time interval among the multiple time intervals.

16. A computing device comprising:
at least one processor; and
memory storing instructions that, when executed by the at least one processor, cause the at least one processor to perform operations comprising:
identifying first data indicative a flux of photons detected by an array of detectors over time, the photons being emitted from a source and at least partially transmitted through a field-of-view (FOV);
identifying second data indicative of a position of an attenuator over time, the position of the attenuator changing over time and being disposed between the FOV and the array of detectors; and
generating an image of the FOV based on the first data and the second data.

17. The computing device of claim 16, wherein the first data is indicative of:
a first amount of the photons received by a particular detector among the array of detectors during a first time interval; and
a second amount of the photons received by the particular detector during a second time interval,
wherein the second data is indicative of:
a first position of the attenuator during the first time interval; and
a second position of the attenuator during the second time interval, the second position being different than the first position, and
wherein generating the image of the FOV is based on the first amount, the first position, the second amount, and the second position.

18. The computing device of claim 16, wherein generating the image of the FOV comprises:
determining, based on the first data, a first number of the photons received by a particular detector among the detectors during a first time interval that comprises a first time;
determining, based on the first data, a second number of the photons received by the particular detector during a second time interval that comprises a second time;
determining a first difference between the first number and the second number;
determining a second difference between the first time and the second time;
determining a quotient comprising the first difference divided by the second difference; and
generating the image based on the quotient.

19. The computing device of claim 16, wherein generating the image of the FOV comprises:
generating, based on the first data, a derivative of the flux of the photons with respect to time; and
generating the image based on the derivative of the flux.

20. The computing device of claim 16, wherein generating the image comprises:
- generating, based on the position of the attenuator over time, a systems matrix (P) comprising sensitivities of the detectors to regions of the FOV, the regions of the FOV corresponding to pixels or voxels of the image;
- generating a data array (g) comprising the amount of the photons detected by the detectors during each of multiple time intervals; and
- determine an image array (f) based on the following equation:

$Pf=g$, and

- wherein f comprises values of the pixels or voxels of the image.

* * * * *